United States Patent
Davidner et al.

(10) Patent No.: US 7,753,869 B2
(45) Date of Patent: *Jul. 13, 2010

(54) REMOVAL AND DEACTIVATION OF VIRUSES FROM BLOOD

(75) Inventors: Alan A. Davidner, Yorba Linda, CA (US); Kimberly A. Walker, Huntington Beach, CA (US); Scott R. Mallett, Coto De Caza, CA (US)

(73) Assignee: Hemavation, LLC, Tustin, CA (US)

( * ) Notice: Subject to any disclaimer, the term of this patent is extended or adjusted under 35 U.S.C. 154(b) by 580 days.

This patent is subject to a terminal disclaimer.

(21) Appl. No.: 11/739,574

(22) Filed: Apr. 24, 2007

(65) Prior Publication Data

US 2007/0190050 A1  Aug. 16, 2007

Related U.S. Application Data

(63) Continuation of application No. 10/390,558, filed on Mar. 17, 2003, now Pat. No. 7,207,964.

(51) Int. Cl.
| | |
|---|---|
| A61M 37/00 | (2006.01) |
| C02F 1/44 | (2006.01) |
| B01D 11/00 | (2006.01) |
| B01D 61/00 | (2006.01) |

(52) U.S. Cl. ............ 604/6.08; 604/5.04; 604/6.01; 604/6.09; 604/6.13; 210/645; 210/650

(58) Field of Classification Search .......... 604/4.01, 604/5.01, 5.04, 6.01, 6.09, 6.13; 422/44; 210/645, 650, 663, 805, 774

See application file for complete search history.

(56) References Cited

U.S. PATENT DOCUMENTS

| 2,886,771 A | 5/1959 | Vincent |
|---|---|---|
| 3,482,575 A | 12/1969 | Claff et al. |

(Continued)

FOREIGN PATENT DOCUMENTS

JP  406285159 A  10/1994

OTHER PUBLICATIONS

DiGiovine, Bruno et al. "The Attributable Mortality and Costs of Primary Nosocomial Bloodstream Infections in the Intensive Care Unit" American Journal of Respiratory and Critical Care Medicine, vol. 160, 1999: pp. 976-981.

(Continued)

Primary Examiner—Leslie R Deak
(74) Attorney, Agent, or Firm—Knobbe, Martens, Olson & Bear, LLP

(57) ABSTRACT

A method and apparatus for preventing and treating septicemia in patient blood is provided. The extracorporeal system includes an antimicrobial device to inactivate at least 99% of bloodborne microorganisms, a hemoconcentrator/filtration unit to remove approximately 50-75% of target molecules from the patient blood and a filter unit to remove target molecules from patient blood from the sieved plasma filtrate. Target molecules are produced by microorganisms, as well as by the patient's cells. These molecules include endotoxins from Gram negative bacteria, exotoxins from Gram negative and Gram positive bacteria, as well as RAP protein mediator from *Staphylococcus aureus*, and cell mediators such as tumor necrosis factor-alpha, and interleukin 1-beta, interleukin 6, complement proteins C3a and C5a, and bradykinin.

18 Claims, 15 Drawing Sheets

U.S. PATENT DOCUMENTS

| | | | |
|---|---|---|---|
| 3,797,485 | A | 3/1974 | Urquhart |
| 4,059,095 | A | 11/1977 | Grundmann et al. |
| 4,061,141 | A | 12/1977 | Hyden et al. |
| 4,181,132 | A | 1/1980 | Parks |
| 4,191,182 | A | 3/1980 | Popovich et al. |
| 4,321,918 | A | 3/1982 | Clark, II |
| 4,322,275 | A | 3/1982 | Jain |
| 4,350,156 | A * | 9/1982 | Malchesky et al. ......... 604/6.04 |
| 4,381,004 | A | 4/1983 | Babb |
| 4,464,166 | A | 8/1984 | Edelson |
| 4,475,900 | A | 10/1984 | Popovich et al. |
| 4,479,798 | A | 10/1984 | Parks |
| 4,540,401 | A | 9/1985 | Marten |
| 4,559,034 | A | 12/1985 | Kirita et al. |
| 4,563,170 | A | 1/1986 | Aigner |
| 4,576,143 | A | 3/1986 | Clark, III |
| 4,657,490 | A | 4/1987 | Abbott |
| 4,670,007 | A | 6/1987 | Wheeldon et al. |
| 4,680,122 | A | 7/1987 | Barone |
| 4,683,889 | A | 8/1987 | Edelson |
| 4,692,138 | A | 9/1987 | Troutner et al. |
| 4,708,715 | A | 11/1987 | Troutner et al. |
| 4,737,140 | A | 4/1988 | Lee et al. |
| 4,769,132 | A | 9/1988 | Patono |
| 4,800,022 | A | 1/1989 | Leonard |
| 4,950,225 | A | 8/1990 | Davidner et al. |
| 4,952,812 | A | 8/1990 | Miripol et al. |
| 4,955,857 | A | 9/1990 | Shettigar |
| 5,041,079 | A * | 8/1991 | Takashima et al. ......... 604/5.02 |
| 5,104,373 | A | 4/1992 | Davidner et al. |
| 5,288,605 | A | 2/1994 | Lin et al. |
| 5,433,738 | A | 7/1995 | Stinson |
| 5,459,030 | A | 10/1995 | Lin et al. |
| 5,496,637 | A | 3/1996 | Parham et al. |
| 5,730,713 | A | 3/1998 | Okarma et al. |
| 5,910,252 | A | 6/1999 | Truitt et al. |
| 5,910,307 | A | 6/1999 | Kwak et al. |
| 5,951,509 | A | 9/1999 | Morris |
| 6,039,946 | A | 3/2000 | Strahilevitz |
| 6,042,783 | A | 3/2000 | Nagamatsu et al. |
| 6,193,681 | B1 | 2/2001 | Davidner et al. |
| 6,312,593 | B1 | 11/2001 | Petrie |
| 6,342,157 | B1 | 1/2002 | Hood |
| 6,620,120 | B2 | 9/2003 | Landry |
| 6,626,857 | B1 | 9/2003 | Ohta et al. |
| 7,201,730 | B2 | 4/2007 | Davidner et al. |
| 7,207,964 | B2 * | 4/2007 | Davidner et al. ........... 604/6.08 |
| 7,229,427 | B2 | 6/2007 | Davidner et al. |
| 7,479,123 | B2 | 1/2009 | Briggs |
| 2004/0182783 | A1 | 9/2004 | Walker et al. |
| 2004/0182784 | A1 | 9/2004 | Walker et al. |
| 2004/0185041 | A1 | 9/2004 | Walker et al. |
| 2004/0185426 | A1 | 9/2004 | Mallett et al. |
| 2004/0186407 | A1 | 9/2004 | Walker et al. |
| 2004/0186412 | A1 | 9/2004 | Mallett et al. |
| 2006/0210424 | A1 | 9/2006 | Mallett et al. |

OTHER PUBLICATIONS

Bellomo, Rinaldo et al. "The Effect of Intensive Plasma Water Exchange by Hemofiltration on Hemodynamics and Soluble Mediators in Canine Endotoxemia" American Journal of Respiratory and Critical Care Medicine, vol. 161, 2000: pp. 1429-1436.

Talmor, Mia, M.D. et al. "Relationship of Systemic Inflammatory Response Syndrome to Organ Dysfunction, Length of Stay, and Mortality in Critical Surgical Illness" Arch Surg. vol. 134, 1999: pp. 81-87.

Amura, Claudia R., et al. "Mechanisms Involved in the Pathogenesis of Sepsis Are Not Necessarily Reflected by In Vitro Cell Activation Studies" Infection and Immunity, vol. 66, No. 11, Nov. 1998: pp. 5372-5378.

Wenzel, Richard P., M.D. "Treating Sepsis" New England Journal of Medicine, vol. 347, No. 13, Sep. 26, 2002: pp. 966-967.

Cole, Louise, MBBS, Fficanzca et al. "A Phase II Randomized, Controlled Trial of Continuous Hemofiltration in Sepsis" Critical Care Medicine, vol. 30, No. 1, 2002: pp. 100-106.

Ronco, Claudio, M.D. et al. "A Pilot Study of Coupled Plasma Filtration with Adsorption in Septic Shock" Crit Care Med, vol. 30, No. 6, 2002: pp. 1250-1255.

Bernard, Gordon R., M.D. et al. "Efficacy and Safety of Recombinant Human Activated Protein C for Severe Sepsis" The New England Journal of Medicine, vol. 344, No. 10, Mar. 8, 2001: pp. 699-709.

Murray, Patrick et al. "Renal Replacement Therapy for Acute Renal Failure" American Journal of Respiratory and Critical Care Medicine, vol. 162, 2000: pp. 777-781.

Osarogiagbon, U. Raymond et al. "Reperfusion Injury Pathophysiology in Sickle Transgenic Mice" Blood, vol. 96, No. 1, Jul. 1, 2000: pp. 314-320.

Warren, H. Shaw, M.D. et al. "Risks and Benefits of Activated Protein C Treatment for Severe Sepsis" The New England Journal of Medicine, vol. 347, No. 13, Sep. 26, 2002: pp. 1027-1030.

Stegmayr, Bernd G. "Is There a Future for Adsorption Techniques in Sepsis".Blood Purification, vol. 18, 2000: pp. 149-155.

Asmis, Reto et al. "Vitamin E. Supplementation of Human Macrophages Prevents Neither Foam Cell Formation Nor Increased Susceptibility of Foam Cells to Lysis by Oxidized LDL" Arterioscler Thromb Vascular Biology, Sep. 2000, pp. 2078-2086.

Carr, Anitra C. et al."Potential Antiatherogenic Mechanisms of Ascorbate (Vitamin C) and α—Tocopherol (Vitamin E)" Circulation Research, Sep. 1, 2000, pp. 349-354.

Segerer, Stephan et al. "Chemokines, Chemokin Receptors, and Renal Disease: From Basic Science To Pathophysiologic and Therapeutic Studies" Journal of American Soceity of Nephrology, vol. 11, 2000: pp. 152-176.

Forni, L.G., M.B., Ph.D. and Hilton, P.J., M.D. "Continuous Hemofiltration in the Treatment of Acute Real Failure" The New England Journal of Medicine, vol. 336, No. 18, May 1, 1997: pp. 1303-1309.

Schindler, Ralf et al. "Influencing the Inflammatory Response of Haemodialysis Patients by Cytokiine Elimination Using Large-Pore Membranes" Nephrol Dial Transplant (2002), Editorial Comments. pp. 17-19.

De Vriese, An. S. et al. "Cytokine Removal During Continuous Hemofiltration in Septic Patients" Journal of American Society of Nephrol, vol. 10, 1999: pp. 846-853.

Matic, Goran et al. "Extracorporeal Removal of Circulating Immune Complexes: From Non-Selective to Patient-Specific" Blood Purification, vol. 18, 2000: pp. 156-160.

Roshchupkin, D.K. and Murina, M.A. "Free-Radical and Cyclooxygenase-Catalyzed Lipid Peroxidation in Membranes of Blood Cells Under UV Irradiation" Membrane Cell Biology, vol. 12, No. 2, 1998: pp. 279-286.

Ward, Richard A. et al. "A Comparison of On-Line Hemodiafiltration and High-Flux Hemodialysis: A Prospective Clinical Study" Journal of American Society of Nephrol, vol. 11, 2000: pp. 2344-2350.

Depner, Thomas, M.D. et al. "Lessons from the Hemodialysis (HEMO) Study: An Improved Measure of the Actual Hemodialysis Dose" American Journal of Kidney Diseases, vol. 33, No. 1, Jan. 1999: pp. 142-149.

Gunn, A. et al. "The Destruction of Peripheral-Blood Lymphocytes By Extracorporeal Exposure To Ultraviolet Radiation" *Immunology*, 50:477-485 (Jun. 6, 1983).

Kupin, V.I. et al. "The Effect of Nondamaging Intensity Laser Irradiation On the Immune System" *Neoplasma*; 34:3,325-330 (1987).

McDougal, J.S. et al. "Thermal Inactivation of the Acquired Immunodeficiency Syndrome Virus, Human T Lymphotropic Virus-III/Lymphadenopathy-Associated Virus, with Special Reference to Antihemophilic Factor" *Journal of Clinical Investigation*, 76:875-877 (Aug. 1985).

Spire, B. et al. "Inactivation of Lymphadenopathy-Associated Virus by Heat, Gamma Rays, and Ultraviolet Light" *The Lancet*, 188-189 (Jan. 26, 1985).

* cited by examiner

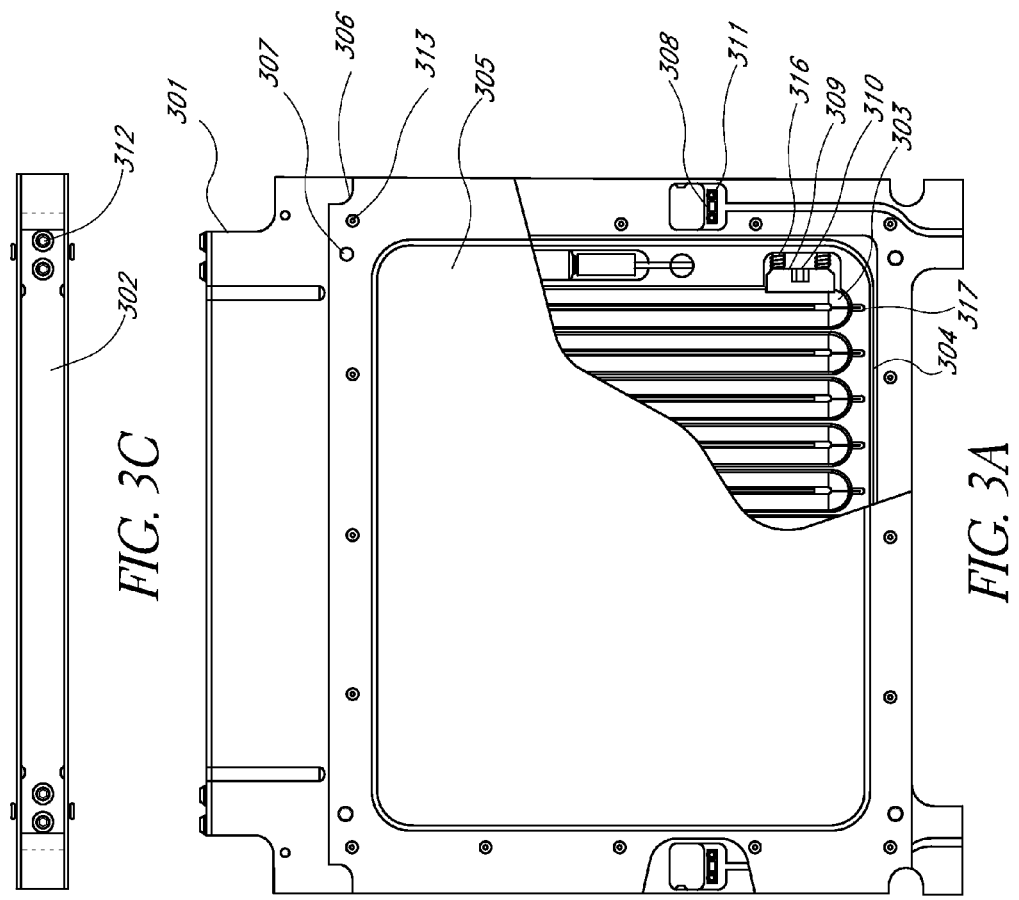
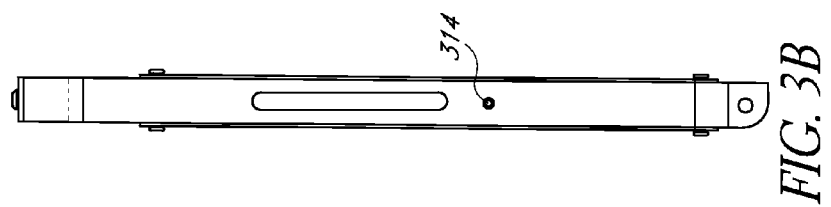

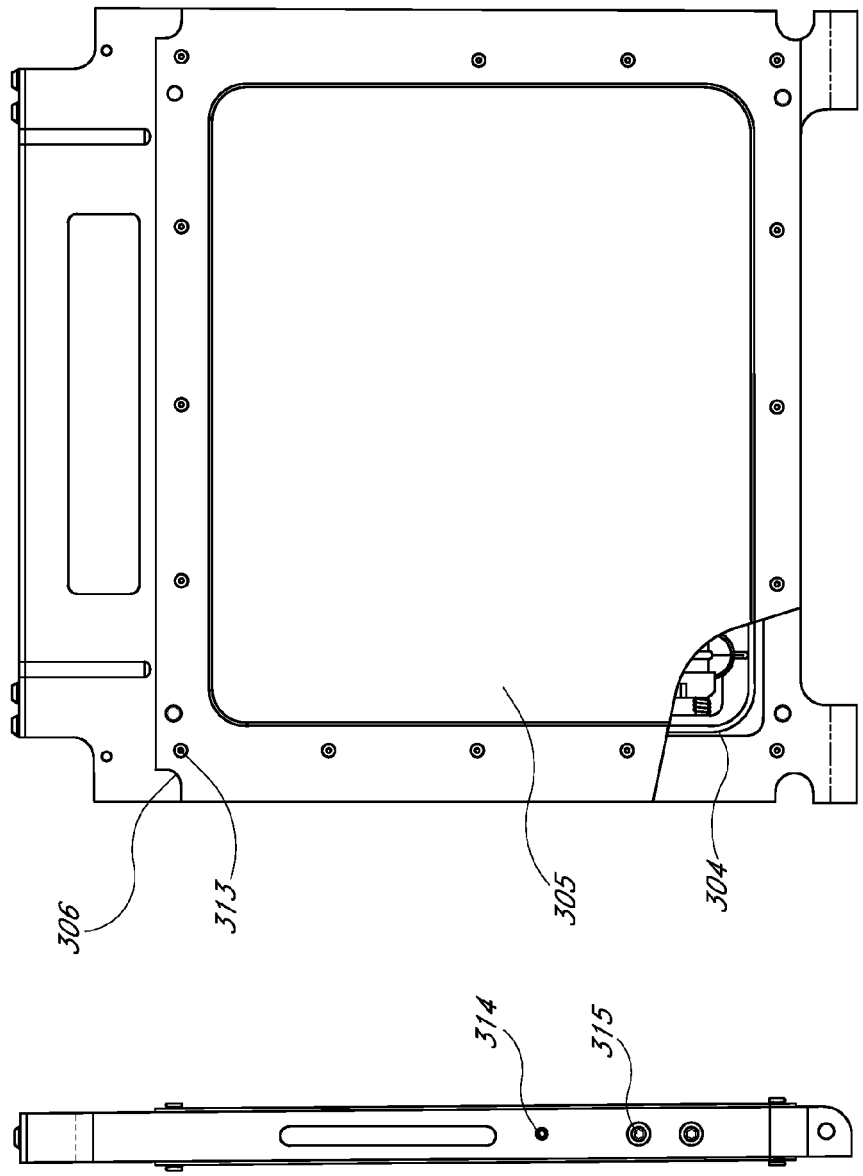

REMOVAL AND DEACTIVATION OF VIRUSES FROM BLOOD

CROSS REFERENCE TO RELATED APPLICATION

This application is a continuation of U.S. application Ser. No. 10/390,558, which was filed on Mar. 17, 2003, now U.S. Pat. No. 7,207,964, which issued on Apr. 24, 2007, the disclosure of which is incorporated by reference.

BACKGROUND

1. Field of the Invention

The present invention relates generally to methods and apparatus for inactivating bloodborne microorganisms. This invention relates to methods and apparatus for removing target molecules from the blood by a hemoconcentrator/filter and for subsequently removing target molecules from the ultrafiltrate by additional filtration for endotoxins and cell mediators before returning the treated blood to the patient. Ultraviolet irradiation is used in some aspects of the invention.

2. Description of the Related Art

Septicemia refers to a microbe-induced condition in which the patient experiences an exaggerated inflammatory response. This response can lead to varying degrees of hypotension (possibly shock), and hypoxemic and edema-related organ failure called multiple organ dysfunction syndrome (MODS). Because trauma and burns, among other causes, can lead to MODS, in the absence of infection, the more current and generic term is systemic inflammatory response syndrome (SIRS).

Between 1980 and 1992 the death rate due to septicemia increased 83% from 4.2 to 7.7 per 100,000 population. The greatest increases were seen in patients at least 65 years old. Bacterial infections accounted for approximately 200,000-300,000 cases of septicemia as of 1992, and was the thirteenth leading cause of death nationally. In 1992, the mortality rate averaged 35%, with a range of 20-65%, and accounted for approximately 100,000 deaths. Now, the average mortality rate has increased to about 200,000 deaths per year, and is the tenth leading cause of death in the United States. There are now 1.5 million cases of sepsis worldwide. This number is expected to increase to 2.2 million in the next ten years.

Septicemia is usually categorized by the particular group of microorganism involved, i.e., bacterial, Gram negative or Gram positive, and fungal. Gram negative bacteria of concern include *Pseudomonas aeruginosa, Eschericia coli,* and *Enterobacter aerogenes*. Gram positive bacteria of interest include *Staphylococcus aureus, Streptococcus pneumoniae,* and *Enterococcus* spp. The usual fungus involved is the yeast, *Candida* spp. Septicemia and related conditions develop when certain microorganisms, the cellular products, and other target molecules stimulate cascade reaction and an exaggerated inflammatory response leading to multiple organ and system failure. Selected microbial products and other target molecules, with molecular weights, are shown in Table 1.

TABLE 1

| Pro-Inflammatory Mediators | Size | Anti-Inflammatory Mediators | Size |
|---|---|---|---|
| IL-1B | 17 kD | IL-1ra | 25 kD |
| IL-6 | 26 kD | IL-1RtypeII | 68 kD |
| TNF-α | 17-54 kD | IL-4 | 15 kD |
| IL-2 | 15 kD | IL-10 | 40 kD |
| IL-12 | 44 kD | IL-13 | 10 kD |
| IL-8 | 8 kD | | |
| C3a | 8 kD | | |
| C5a | 9 kD | | |
| LBP | 55 kD | | |
| MIF | 12 kD | | |
| IFN | 17 kD | | |
| LIF | 20 kD | | |
| VCAM | 80 kD | | |
| ICAM-1 | 90 kD | | |
| LPS | 10-100 kD | | |

These target molecules may enhance the microbe's virulence and/or stimulate the patient's defense mechanisms, but, when excessive, they may lead to multiple organ system failure. These microorganisms, their cellular products and the target molecules can stimulate various cascade reactions which may result in a life-threatening inflammatory disease state.

Prevention of these medical conditions is difficult at best because the early signs and symptoms may be quite vague. Treatment has generally been instituted when the condition is recognized which is, unfortunately, often very late in the course of the disease. With prophylaxis difficult and therapy often late, the results may be fatal for the patients in many cases.

Ultraviolet blood irradiation, originally the Knott technique, has been used in the United States since 1928 for the successful extracorporeal treatment of microbial infections. Over the years there have been scientific arguments concerning the mechanism by which ultraviolet blood irradiation ("UBI") works, and the consensus appears to be that some organisms are inactivated. It is believed that UV light radiation of range "C", or UV-C, stimulates the immune system to become more efficient at clearing the remaining organisms from the body.

Hemoconcentrator/filtration units are used to remove water from patients who are in acute renal failure and become overly hydrated. The devices are designed to retain the majority of plasma proteins, including one of the smallest, albumin, (molecular weight of 67-69 kD), while ridding the blood of excess water. Current membranes and/or hollow fiber systems have effective pore sizes which will pass molecules up to 30-50 kD.

SUMMARY OF THE INVENTION

It is one object of the present invention to provide a blood treatment system to inactivate bloodborne microorganisms. In one aspect, a method and apparatus is provided for removing target molecules from the blood by a hemoconcentrator/filter and for subsequently removing target molecules from the ultrafiltrate by additional filtration for endotoxins and cell mediators before returning the treated blood to the patient. Ultraviolet irradiation is used in some aspects of the invention.

It is one object of the present invention to remove blood from a patient, or obtain blood from a source, and to provide a diluent source for supplying a diluent to reduce the hematocrit of the blood. In one aspect, the diluent source supplies a diluent which reduces the blood to a hematocrit of about 5% to about 20%. A concentrator device to receive blood is provided to filter the blood and to remove the diluent. A return path connected for returning filtered blood from said concentrator device to a blood source. In one aspect, the return path includes tubing and/or a single lumen cannula.

It is another object to provide a recycle path connected for returning the diluent removed from the blood by the concentrator device to said diluent source. In one embodiment, the recycle path comprises a filter. In one aspect, the recycle path includes a membrane module and/or a recycle pump.

It is one object of the invention to provide a filter device connected to receive blood from the source and to supply a portion of the blood to an irradiator or to another filter and to return the remainder of the received blood to the source. It is a further object to provide a reservoir connected to receive material filtered from the blood by the concentrator device.

It is a further object to provide a system and method to treat blood using two types of filters. In one embodiment, the first filter is a hemoconcentrator filter having a porosity of about 70-90 kilodaltons. In one aspect, the first filter is made of polysulfone fibers. The second filter is a cytokine filter having a porosity of about 10-30 kilodaltons. In one aspect, the second filter includes two filters connected in parallel, each filter having a porosity of about 10-30 kilodaltons. In one embodiment, the second filter has a porosity of about 10 kilodaltons.

In one aspect of the invention, the concentrator device has a membrane or filter having a transmembrane pressure greater than 76 mmHg. In one aspect, the concentrator device includes two hemoconcentrators connected in series. In some aspects, each hemoconcentrator is connected to a separate hemoconcentrator pump. In one aspect, the concentrator device filters the blood received thereby by the size of the constituents of the blood. In one embodiment, the concentrator device includes a hollow cylinder and a central core formed of hollow fibers axially disposed within the hollow cylinder. In one aspect, the hollow cylinder has a length of about 10 inches and a diameter of about 1.5 inches, and the central core has a surface area in the range of between about $1.2 \text{ m}^2$ to about $2.4 \text{ m}^2$. It is one object of the present invention to provide an inlet monitoring means at the concentrator device for monitoring the pressure of the blood.

It is one object of the current invention to provide a system and method for treating blood using a device having a concentrator or first filter that has a transmembrane pressure (TMP) that is greater than 76 mmHg. The range of TMP is as follows: about 80 mmHg to about 85 mmHg, about 86 mmHg to about 95 mmHg, about 96 mmHg to about 105 mmHg, and greater than about 105 mmHg.

It is yet another object of the invention to provide at least one pump connected to said system for moving blood, diluent or other fluid through the system. In another aspect of the invention, the combined blood/diluent flow rate is less than 400 mL/min. The range of the combined flow rate is as follows: about 75 mL/min to about 125 mL/min, about 126 mL/min to about 200 mL/min, about 201 mL/min to about 300 mL/min and about 301 mL/min to about 400 mL/min. In one aspect, the blood flow rate alone is about 50 mL/min to about 300 mL/min, preferably about 100 mL/min.

It is another object of the invention to provide an oxygenator 105 connected between the source and said filter device in order to oxygenate the blood received from the source.

It is a further object to provide a heater to warm at least a portion of the blood or a heat exchanger to cool at least a portion of the blood. In one embodiment, blood is heated or cooled by about 1-10° C.

It is one object of the current invention to further provide a UV irradiation device to irradiate blood. In one aspect, the UV irradiation device receives and irradiates blood containing biological toxins from a source of blood. In one embodiment, the irradiator device includes a UV light source and a fluid chamber adjacent to the UV light source, where the fluid chamber confines the fluid to a thin film for exposure to the UV light source. In one aspect, the UV light source delivers ultraviolet radiation to the blood in a dose ranging from about $2 \text{ mW/cm}^2$ to about $20 \text{ mW/cm}^2$. In another aspect, the effective dose of ultraviolet radiation applied to the blood is about $1 \text{ mW/cm}^2$ to about $19 \text{ mW/cm}^2$. In one aspect, the fluid chamber is a bag for holding the diluted blood, the bag having a length in the range of about 15 inches to about 20 inches, a width in the range of about 8 inches to about 10 inches, and a fluid path having a width of about 0.75 inches to about 1 inch. In one aspect, a sensor is provided to monitor ultraviolet radiation emitted by the irradiator device.

It is one object of the invention to provide a system and method to treat a patient having an inflammatory disease. Inflammatory diseases include, but are not limited to, sepsis, acute renal failure, ischemic stroke, Sudeck's syndrome, chronic fatigue syndrome, heat stroke, Hodgkin's Disease, lupus, myocardial infarction, AIDS, viremia, HCV, HBV, tuberculosis, muscular dystrophy or multiple sclerosis, Acute Respiratory Distress Syndrome, and heart disease.

It is yet another object of the invention to provide a system and method of reducing free radicals in a patient's blood. In one embodiment, one or more free radical quenchers are added to the blood prior to, during and/or after treatment with the concentrator/filter embodiments described herein. Quenchers are administered directly to the patient and/or are added to the various components of the concentrator/filter embodiments, including, but not limited to, the tubing, the pump, the filters and the diluent source so that the blood can be exposes to the quenchers while being concentrated or filtered. In one embodiment, the quencher is an antioxidant. Quenchers used in several embodiments of the present invention include, but are not limited to, Zn, Cu, manganese, selenium, vitamin A, C, E, B complex, K, P, lycopene, superoxide dismutase, co-enzyme Q10, catechins, polyphenols, flavanols, depsides (chlorogenic acid, coumaroylquinic acid or theogallin), quinic acids, carotenoids, thearubigens, theaflavin, theaflavic acids and ethyl pyruvate. In one embodiment, a cocktail of vitamin A, vitamin C, vitamin E and zinc is used. Quenchers are provided in a dose sufficient to reduce the concentration of one or more free radicals in the blood.

It is a further object of the instant invention to provide a system and method of reducing toxins in a patient's blood using vitamin therapy. These vitamins include the free radical quenchers and antioxidants described above, and include several vitamins which exert their action by reducing the concentration of toxins, including, but not limited to bacteria, viruses, free radicals and inflammatory mediators, in the blood. In one embodiment, vitamins are added to the blood prior to, during and/or after treatment with the concentrator/filter embodiments described herein. Vitamins are administered directly to the patient and/or are added to the various components of the concentrator/filter embodiments, including, but not limited to, the tubing, the pump, the filters and the diluent source so that the blood can be exposed to the vitamins while being concentrated or filtered using this system.

It is another object to provide a system and method of treating blood by using a hemoconcentrator/filter system in conjunction with administering a drug in a dose sufficient to facilitate cellular glucose entry. In one embodiment, insulin therapy is provide to regulate glucose levels.

It is a further object to provide a system and method of treating blood by using a hemoconcentrator/filter system in conjunction with administering a drug in a dose sufficient to facilitate microcirculation and organ oxygenation. In one embodiment, nitroglycerin is provided to the patient to increase microcirculation.

It is yet another object to provide a system and method of down-regulating a patient's immune system by removing one or more immune system mediators from the patient's blood. In one embodiment, blood is obtained from a patient and diluted to reduce the hematocrit of the blood. The diluted blood is then filtered to reduce concentration of at least one immune system mediators from the diluted blood. The blood is also concentrated to remove the diluent from the blood. The treated blood is then reintroduced into the patient. Because one or more immune system mediators is removed from the treated blood, the patient's immune system is down-regulated. In one aspect, the immune system mediator is an inflammatory mediator. In one embodiment, the concentration of at least one inflammatory mediator is reduced by about 75% in less than about 4 hours. In one embodiment, the concentration of TNF-α is reduced by about 50% in less than about 4 hours. Inflammatory mediator include, but are not limited to, TNF-α, IL-1β, IL-6, IL-8, IL-10, IL-12, LPB, IFNγ, LIF, MIF, MCP-1, C3-a, C5-a, exotoxins and endotoxins. In some embodiments, the immune system is down-regulated using a transmembrane pressure greater than 76 mmHg. In another embodiment, a flow rate of less than 40 mL/min is used. Filter and hemoconcentrators, described above, are used to down-regulate the immune system in many embodiments. In several embodiments, irradiation, free radical quenchers, vitamin therapy, insulin therapy and/or nitroglycerin, as described herein, are used in conjunction with or to facilitate immune system down-regulation.

It is yet another object of the present invention to provide a device for treating blood using three pumps, a blood pump, a diluent pump and a hemoconcentrator pump. In this embodiment, referred to as "the HemaCharge device," a load cell to maintain proper hemodilution and hemoconcentration of patient blood is provided. The user interface is a backlit LCD touch screen display. The device also incorporates clamps, a bubble detector, pressure sensors, temperature sensors, a UV sensor, as well as visual and audible alarms for patient safety. Also provided is a power supply module containing an isolation transformer, a solid-state electronic ballast, and associated electronics to produce about 5-24 VDC to power the pumps, clamps, and sensors. A strain gauge beam type load cell is provided to measure the weight of the diluent bag. A 70-90 kD polysulfone hollow fiber filter used for hemoconcentrating dilute blood and two 10 kD polysulfone hollow fiber filters for cytokine removal are also provided. An ultraviolet irradiator lamp assembly is also provided. The UV irradiator assembly is used to irradiate dilute extracorporeal blood with 254 nm UV-C energy. The assembly comprises a 200 W UVC grid lamp and lamp support structure, two quartz glass plates and compression plates to constrain the diluted blood in the irradiator bag to approximately 0.025" thickness. UV-C and temperature sensors are used to optimize ultraviolet output of the bulb. A safety interlock switch is provided to prevent unwanted user exposure to UV-C when loading/unloading the disposable set of materials. Five pressure sensors are used; one each on the patient inlet and return lines, one before the irradiator bag assembly inlet, one at the hemoconcentrator inlet, and one located between the hemoconcentrator ultrafiltrate outlet and the concentrator pump. The inlet pressure sensor can be used to determine maximum allowable blood flow rate based on vascular access and catheter placement parameters; the patient return line sensor can likewise indicate catheter placement issues on the return side, as well as provide a measure of safety against excessive return pressures. The sensor located before the irradiator bag assembly provides an indication of bag pressure and is used to prevent over pressurization of the irradiator bags. The sensors located at the inlet and ultrafiltrate outlet of the hemoconcentrator as well as the patient return sensor are used to determine hemoconcentrator TMP. TMP is used to determine appropriate blood flow rates and to determine adequate performance of the hemoconcentrator. Visual and audible alarms are provided for out-of-range pressures.

It is another object of the present invention to provided manual and/or automated mechanisms of control for several embodiments described herein. In one embodiment, on-line pressure monitors or optical devices aid a technician in regulating hematocrit. In other embodiments, monitoring and regulation of hematocrit is automated using an electronic weight scale, or load cell, which measures the volume or mass of diluent. Computer hardware and software is also used in various embodiments.

BRIEF DESCRIPTION OF THE DRAWINGS

FIGS. 3A-3E show various views of one embodiment of the UV system.

DETAILED DESCRIPTION OF SOME PREFERRED EMBODIMENTS

Figure 1:
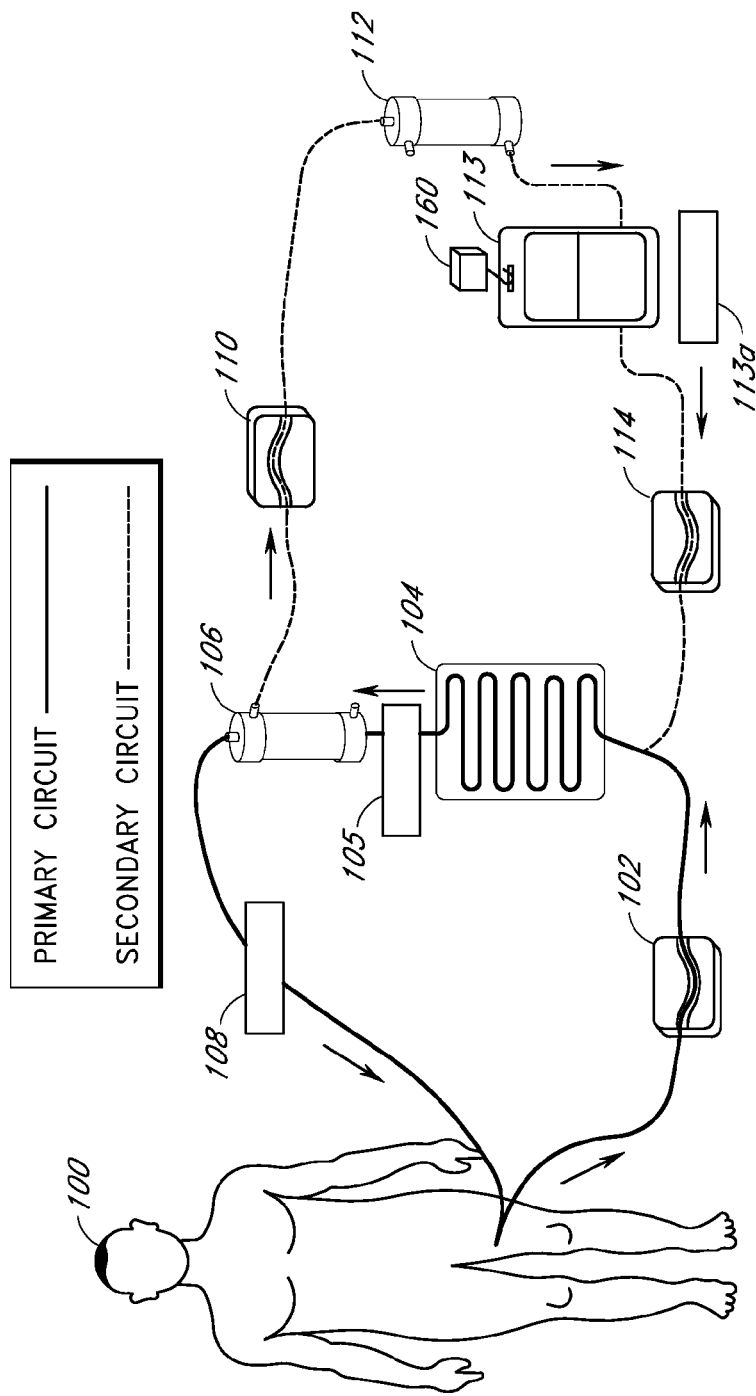
FIG. 1 is a schematic representation of one embodiment of the system of the instant invention.

FIG. 1 shows a schematic representation of one embodiment of the present invention. In one embodiment, blood is pumped from the patient 100 at a flow rate of about 100-300 mL/min, using a blood pump 102. One of skill in the art will understand that blood can also be pumped at a flow rate less than about 50 mL/min and at a rate greater than about 300 mL/min. A blood flow rate of less than about 50 mL/min may lead to clotting in certain cases. A blood flow rate of greater than 300 mL/min may not be supported by certain hypovolemic and/or hypotensive patients and may lead to venous stenosis or collapse.

Blood is diluted using diluent pump 114 to adjust the hematocrit to about 10%, and then circulated into a bag within the UV irradiator 104. The irradiated blood then flows towards the 70-90 kD filter 106, which removes an ultrafiltrate containing molecules less than about 90 kD in weight. Through removal of the ultrafiltrate, the cellular blood elements are restored to their original concentration before returning the blood to the patient. The ultrafiltrate is pumped through a 10 kD filter 112 using a hemoconcentrator pump 110, where molecules greater than about 10 kD are retained, and those less than about 10 kD are allowed to pass through and into the diluent source or reservoir 1131 where they become available for mixing with blood that is being removed from the patient. At the end of the approximately 3-hour procedure, much of the whole blood extracorporeal volume is returned to the patient 100 in an attempt to preserve total red cell volume.

Because most pro-inflammatory/anti-inflammatory mediators have a molecular weight of 10 to 90 kD, it is expected that about 50-75% of immune system mediators will be removed from blood after about 3 hours of treatment. In several embodiments, reduction of target molecules is accompanied by substantial irradiation-induced bacterial reduction. In one embodiment, the TNF-α trimer, the principal form in blood with a molecular weight of about 45-55 kD, will be removed by this method.

In one embodiment of the present invention, a system to reduce bacterial load in septic patients is provided. Diagnosis and prevention of septicemia and related conditions is difficult because the early signs and symptoms are usually vague. Because these conditions are typically recognized late in the course of the disease, morbidity and mortality rates are unduly increased. In one embodiment, bacterial load is reduced by about 99%. In several aspects of this invention, septicemia is prevented or treated in patients undergoing coronary bypass, dialysis and other conditions. In one embodiment, the system disclosed herein can be used to prevent or treat septicemia in patients undergoing any invasive procedure. In several embodiments, the device described herein can prevent and/or treat systemic inflammatory response syndrome by any etiology, including, but not limited to septicemia or microbial sepsis. In one embodiment, patients with acute renal failure can be treated. In another embodiment, patients with ischemic stroke can be treated.

In one embodiment of the invention, a prevention and treatment system for Sudeck's Syndrome is provided. Sudeck's Syndrome, also known as Reflex Sympathetic Dystrophy, is characterized by acute atrophy of bones, commonly of the carpal or tarsal bones. Biochemical mediators and an excessive inflammatory reaction are involved in the etiology and progression of this disease. (Cook and Ward, 1990; Goris, 1998, both herein incorporated by reference). In one embodiment, a hemoconcentrator/filter system is used to remove target molecules from the blood of a patient afflicted with Sudeck's Syndrome. Molecules targeted for removal include, but are not limited to, prostaglandins, endothelium-derived relaxing factor and histamine. One skilled in the art will understand that other cell mediators involved in this syndrome can also be removed in accordance with several embodiments of the present invention.

In a related embodiment, a hemoconcentrator/filter system is used to remove target molecules from the blood of a patient afflicted with Chronic Fatigue Syndrome. Molecules targeted for removal include, but are not limited to, TNF-α, IL-6 and other cytokines. One skilled in the art will appreciate that other cell mediators involved in Chronic Fatigue Syndrome can also be removed in accordance with several embodiments of the present invention.

In addition to removing tumor necrosis factor, or TNF-α, from patients with Chronic Fatigue Syndrome, other embodiments of the present invention provide a system for reducing TNF-α levels, and/or other immune system mediators, in any illness in which these mediators are involved in the etiology or progression of the disease.

In other embodiments, a prevention and treatment system for other inflammatory related diseases is provided. These diseases include, but are not limited to, heat stroke, Hodgkin's Disease, lupus, myocardial infarction, AIDS, viremia, HCV, HBV, tuberculosis, muscular dystrophy or multiple sclerosis, Acute Respiratory Distress Syndrome (ARDS), and heart disease.

Transmembrane Pressure (TMP)

Hemoconcentrator transmembrane Pressure (TMP) is calculated as (Inlet Pressure+Outlet Pressure/2)−Ultrafiltration Pressure. In a preferred embodiment, TMP is kept below about 400 mmHg for maximum filter performance. Exceeding this maximum TMP may result in filter failure (i.e., a clogged filter) which could potentially send clots back to the patient. However, one skilled in the art will appreciate that under certain conditions, a TMP greater than about 400 mmHg can be used. The range of TMP used in one embodiment of this system is about 1-400 mmHg. TMP typically depends on factors such as entering HCT, exiting HCT and blood flow rate. In one embodiment, the TMP is between about 1-200 mmHg, preferably between about 9-105 mmHg. Typically, at a constant flow rate, a decrease in hematocrit results in a lesser pressure drop and lower inlet pressure, while an increase in hematocrit results in a greater pressure drop and higher inlet pressure. Thus, changes in inlet pressure signal changes in hematocrit. Thus, in one embodiment, on-line pressure monitors or optical devices can aid a technician in regulating hematocrit. In other embodiments, monitoring and regulation of hematocrit is automated using a load cell, described below.

In U.S. Pat. No. 6,193,681, we described a method and apparatus for inactivating bloodborne microorganisms by ultraviolet irradiation. In that system, the pressure across the hemoconcentrator was designed to decrease 70-100 mmHg from inlet port to outlet port. The TMP of the original system was about 50-75 mmHg. In the present invention, a design in which the pressure across the hemoconcentrator decreases 1-69 mmHg and in which the TMP is greater than about 76 mmHg provided surprising and unexpected advantages. For example, hemoconcentration was achieved more efficiently allowing a higher flux rate which translates into greater target molecule sieving. More importantly, using a TMP greater than about 76 mmHg and a blood flow rate of about 100 mL/min allows processing of blood with a hematocrit of greater than about 36%. The system disclosed in U.S. Pat. No. 6,193,681 was able to process blood having a hematocrit less than about 35%. Embodiments of the current invention are particularly advantageous because it is estimated that over 20% of septic patients have a hematocrit that exceeds 35%. Moreover, a system which uses a TMP greater than 76 mmHg also provides a novel and unique method of treating several other disorders in which hematocrit exceeds 35%. In particular, about 50% of patients with renal failure, 99% of stroke patients and 99% of patients with autoimmune disorders have blood hematocrit levels that are greater than 35%. These patients would greatly benefit from a system which was capable of inactivating life-threatening microorganisms in their bloodstream. Embodiments of the current system, which use a TMP of greater than about 76 mmHg, offers this treatment opportunity to these patients. Indeed, using a TMP that is greater than 76 mmHg with a blood flow rate that is greater than 100 mL/min allows treatment of septic patients that have a hematocrit less than 36%.

In one embodiment, the TMP of the present invention is greater than 76 mmHg, preferably from about 76-150 mmHg, and more preferably from about 76-105 mmHg. TMP ranges from about 76-85 mmHg, 86-95 mmHg and 96-105 mmHg are also provided in accordance with several embodiments of the current invention. As discussed above, a TMP greater than 76 mmHg corresponds to a hematocrit greater than about 36%, a value which represents 20% of septic patients and a large percentage of other patient populations. In one embodiment, blood having a hematocrit of greater than 36% is treated. Hematocrit ranges from about 36% to about 40%, 41% to about 50%, 51% to about 55%, and greater than about 55% are also provided in accordance with several embodiments of the current invention. Ideally, blood treatment provided in several embodiments of the present invention will last about 1-3 hours. However, in an alternate embodiment, a longer treatment can be performed at a slower blood flow rate. This embodiment has particular benefits to a hemodynamically unstable patient. In one embodiment, this system uses a TMP of less than about 50 mmHg and takes more than about 3 hours to accomplish the toxin removal goals.

System Operation—Blood Pump

Blood is received from the patient through a canula placed in the femoral subclavian or internal jugular vein. One skilled in the art will understand that other methods used to withdraw blood from a patient can also be used in accordance with several embodiments of the present invention. In one embodiment, a filter device is connected to receive blood from the source and to supply a portion of the received blood to a UV irradiation device and to return the remainder of the received blood to the source. In one embodiment, a canula is connected to a patient and a tubing is connected to the canula through a pump and into a hollow fiber filter device to receive blood from the source. The pump supplies a portion of the blood to the irradiation device or the concentrator and returns the remainder of the blood back to the patient. In another embodiment of the invention, blood is received from a source. The source includes, but is not limited to, blood that has been previously withdrawn from a patient and stored. The source also includes donated blood taken from one or more healthy individuals, which requires treatment before being available as a donor blood.

When receiving blood from the patient, a blood pump controls the flow rate of the blood in several embodiments. A preferred embodiment of the present invention has three pumps. As shown in FIG. 1, one embodiment has a blood pump 102, a diluent pump 114, and a concentrator pump 110. In one embodiment, blood from pump 102 passes through a polycarbonate "Y" connector where the blood mixes with a suitable isotonic diluent, such as Plasma-Lyte® (Baxter Healthcare, Deerfield, Ill.) solution. A variety of such solutions, referred to as "crystalloids", are available. The diluent is supplied from diluent source 113 which, typically, comprises a large capacity reservoir for storing an admixture of reclaimed (or converted) ultrafiltrate. The diluent is delivered by pump 114, which can be a roller pump or the like, at a flow rate which results in a hematocrit of about 5-20%.

In U.S. Pat. No. 6,193,681, we described a method and apparatus in which the combined blood/diluent pump flow rate was 400-500 mL/min. In several embodiments of the present invention, a design in which the combined pump flow rate is less than 400 mL/min provides unexpected advantages over a flow of greater than 400 mL/min. Surprisingly, the slower combined flow rate is safer and easier to manage on a patient and there is a lower probability of developing cavitation from the blood source catheter (i.e. the arterial catheter). Additionally, greater blood dilution results in a lower protein concentration throughout the system. A higher filtration fraction (filtration fraction=ultrafiltration rate/combined flow rate) results in a higher ultrafiltration (UF)/flux rate. Less protein in the blood solution results in less protein deposition on the surface of the hemoconcentrator. This, in turn, helps retain the integrity of the hemoconcentrator's pore size allowing for more consistent removal of target molecules for longer periods of time. Concurrently, the greater blood dilution allows for increased UF rates, which in turn increase target molecule sieving.

In one embodiment of the present invention, the combined blood/diluent pump flow rate is less than about 400 mL/min, preferably from about 10 mL/min to about 390 mL/min, more preferably from about 200 mL/min to about 380 mL/min. In one embodiment, when using a blood flow rate of about 100 mL/min, the combined blood/diluent flow rate is about 280-380 mL/min.

In one embodiment of the present invention, the ultrafiltrate side of the system is a continuous length of tubing that runs through a pump into a secondary filter. One of skill in the art will understand that material filtered from the blood can be collected in a filtrate collection reservoir in a "closed-loop" system, as described in U.S. Pat. No. 6,193,681, herein incorporated by reference.

System Operation—Diluent Pump

In one embodiment, the concentrator pump 114 propels the admixture of crystalloid and filtrate from the secondary circuit back to the primary circuit via Y-connector. Thus, smaller molecules can be conserved by passage thereof completely through the secondary circuit, while plasma proteins and other large molecules are conserved by retention thereof in the primary circuit at the hemoconcentrator.

Pump flow is initially based on the hematocrit of the patient 100 and can be subsequently regulated with knowledge of hemoconcentrator inlet pressure as determined by an inlet port. That is, a port may include a stopcock for monitoring the inlet pressure and/or for sampling of the fluid. In one embodiment, connection of the components in the secondary circuit is by tubing. One skilled in the art will understand that other connector mechanisms can also be used in accordance with several embodiments of the current invention. In other embodiments, blood pump flow is fixed at about 100 mL/min. In yet another embodiment, the blood pump flow is lowered below 100 mL/min to accommodate hemodynamically unstable patients. In another embodiment, pump flow is regulated using TMP measurements. Blood flow can be monitored manually or via an automated feedback system, based upon TMP values.

In one embodiment of the present invention, only two pumps are used, a combined blood/diluent pump and a concentrator pump. A separate blood pump is not used. A single pump positioned substantially as pump 102 shown in FIG. 1, regulates both patient blood and diluent flows. A pump with the capability of dual raceway control or a traditional single raceway pump coupled with thumb screw control of diluent flow can be used. In the latter case, the "dual" pump flow would be regulated at a flow rate of about 100-1,000 mL/min, accounting for the combined flows from the patient 100 and the diluent reservoir 113.

System Operation—Concentrator Pump

A concentrator pump 110 is shown in FIG. 1. In one embodiment, pump 110 propels blood to a second filter 112. The target molecules are trapped by this second filter 112 with a porosity of about 10-30 kD. For example, endotoxins from the cell wall of Gram negative bacteria containing protein and negatively-charged lipopolysaccharide (LPS) with a molecular weight of about 10-100 kD are captured in filter 112. In one embodiment, about 99% or more of such material is captured. In one embodiment, plasma hemoglobin and myoglobin are also trapped by this filter. In yet another embodiment of this system, the majority of molecules with a molecular weight of less than about 10-30 kD pass through module 112 to the large-capacity diluent reservoir 113 where they mix with crystalloid.

In one embodiment, ultrafiltration occurs in the hemoconcentrator 106 at the pressure drop previously indicated much as it does in the glomerular units of the natural kidney. However, the natural kidney prevents the passage of the small and plentiful plasma protein albumin (67-69 kD molecular weight) and permits occasional passage of free plasma hemoglobin (64 kD molecular weight), thereby demonstrating a sharp cutoff at a molecular weight of about 65 kD. In one embodiment, the hemoconcentrator 106, with 60-95 kD porosity, is effective at prohibiting passage of plasma proteins (less than about 5% of plasma albumin, less than about 2% of plasma globulin sieved) while permitting sufficient passage of electrolytes, BUN, creatinine, myoglobin and glucose to ensure normal plasma osmolality.

In one embodiment, larger molecules, such as plasma hemoglobin, are incompletely sieved (about 25-95% of plasma concentrations). Permeability of target molecules IL-1β, IL-6 and some LPS is about 100% (appearing in the ultrafiltrate in concentrations equivalent to plasma) in one embodiment of this system. TNF-α, with a molecular weight of 17-54 kD, is far less permeable than other molecules similar in size, indicating that factors other than simple molecular weight are important. Thus, in one embodiment, IL-6, IL-1β and some LPS are effectively and efficiently removed by this system in high percentages.

Hemoconcentrator

Figure 1A:
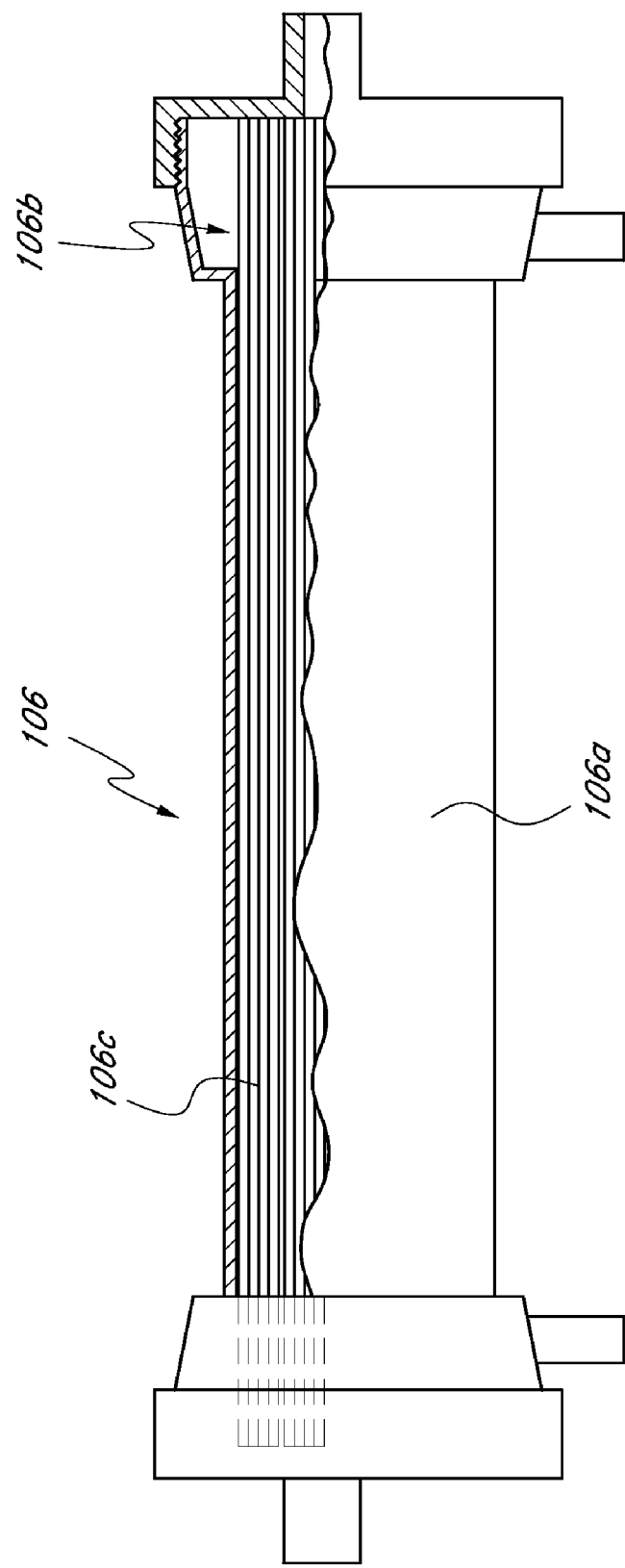
FIG. 1A is a partial cutaway view of an embodiment of a hemoconcentrator.

One or more hemoconcentrators are used in several embodiments of the present invention. The hemoconcentrator 106 is constructed of a hollow cylinder formed 106a (FIG. 1A) of polycarbonate or similar material. The cylinder 106a is, in one embodiment, approximately 10 inches long and about 1.5 inches in diameter. An inlet and an outlet of suitable configuration to be attached to conventional medical tubing are provided in caps and at opposite ends of the cylinder 106a. The caps are typically threadedly attached to the cylinder 106a. In addition, at least one effluent or drainage port is provided adjacent one end of the cylinder 106a. The interior of the cylinder 106a is filled with filter material comprising polysulfone hollow fibers 106c, has a surface area of between about 1.2 $m^2$ to about 2.4 $m^2$ with a pore size of about 70-90 kD and is capable of removing blood proteins and cell mediators whose molecular weight is less than about 85 kD. The embodiment illustrated in FIG. 1A comprises a central core 106b formed of the hollow fibers 106c axially disposed within the hollow cylinder 106a. Because the blood is diluted to about 5% to 20% hematocrit, the gel layer formed by the blood is not thick enough to substantially reduce the effective pore size of the hollow fibers 106c, as it is in conventional hemofiltration techniques. Here, it estimated that the pore size is reduced by about 5% to 20% by the gel layer formed, whereas in traditional hemofiltration techniques, the pore size is reduced significantly more.

In one embodiment, two hemoconcentrators connected in series, are used. Use of two or more hemoconcentrators in series is particularly efficient at reconstituting blood at lower than about 10% hematocrit back to whole blood hematocrit. Additionally, when running the system at slower flow rates (i.e. at lower than about 100 mL/min), the extra surface area provided by two or more hemoconcentrators is helpful in preventing clogging of the filter. Moreover, in some embodiments, a series of hemoconcentrators is better able to share the load of ultrafiltrate removal without exceeding desired filtration fractions. In one embodiment, two concentrator pumps are used to remove the ultrafiltrate. A dual raceway pump can be used in accordance with several embodiments of the current invention. In one aspect of the invention, each concentrator pump is controlled separately, allowing further optimization and control of filtration fraction for each hemoconcentrator. One skilled in the art will understand that more than two hemoconcentrators can be used in accordance with embodiments of this invention.

In one embodiment, a hollow fiber or filter surface area of about 1.2 $m^2$ to about 2.4 $m^2$ is used to provide sufficient area to reconstitute the diluted blood in volumes equivalent to those added to the circuit. Typically, blood returning to a septic patient is not substantially diluted because the patient may experience secondary pulmonary dysfunction.

Ultraviolet Irradiation

In some embodiments of the present invention, it is advantageous to use UV irradiation to inactivate microorganisms. FIGS. 2-6 show several views of a UV irradiator and bag used in some embodiments of the instant invention.

Figure 2:
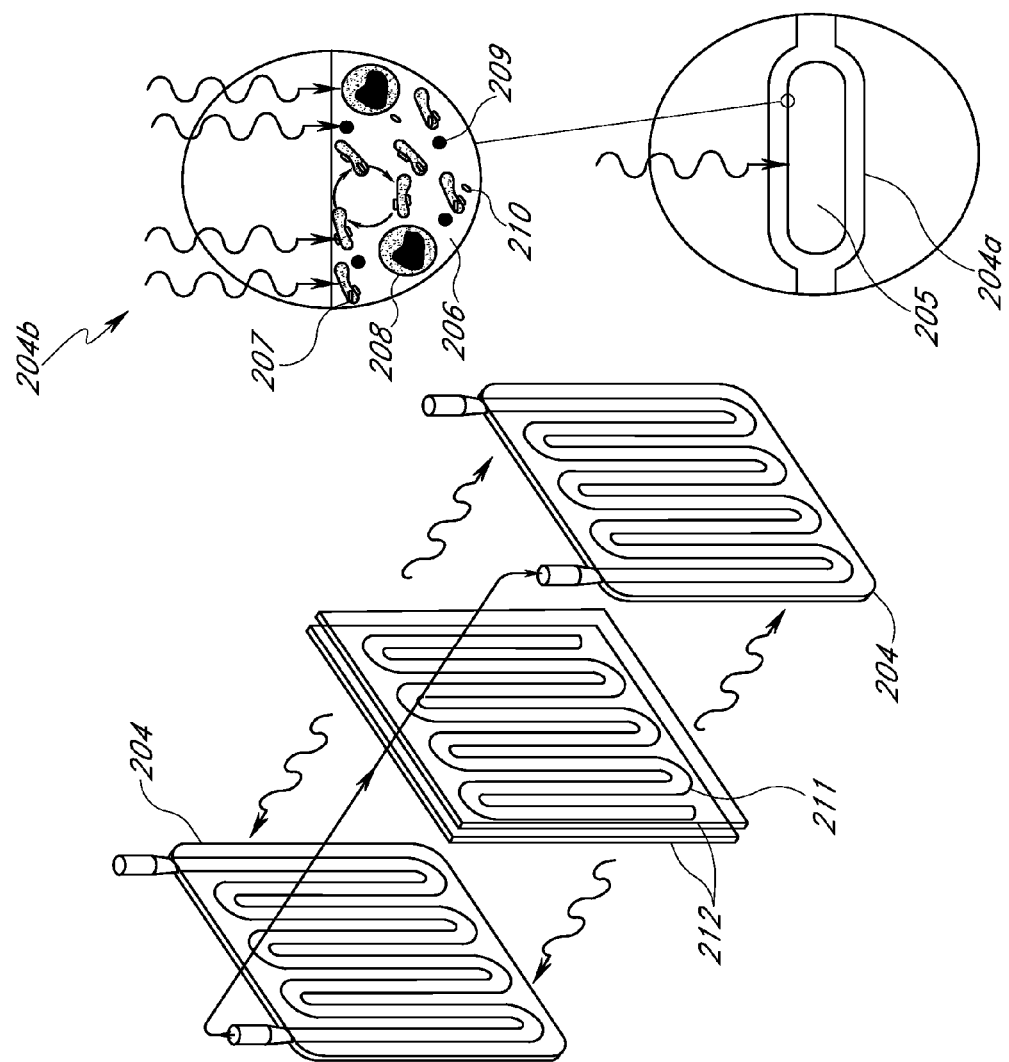
FIG. 2 shows a schematic of one embodiment of the UV irradiator and bag.

In one embodiment, shown in FIG. 2, the irradiator includes a bag 204 and UV channel (grid lamp) 211 shaped in a serpentine path. Two quartz plates 212 used to compress the blood within the bag are also provided. A cross-sectional view 204a of the UV bag 204 and an enlarged view thereof 204b is shown in FIG. 2. A blood flow channel 205 is shown in the cross-sectional view 204a. During treatment, the UV bag contains one or more of the following: plasma 206, red blood cells 207, white blood cells 208, platelets 209 and bacteria 210. In one embodiment, the bag 204 is disposable and made of a biocompatible ethylene vinyl acetate ("EVA") material. In another embodiment, the bag is made of a fluoropolymer. The bag is typically open at each end and with a small inlet therethrough. In one embodiment, the bag 204, or fluid chamber, is approximately 15 to 20 inches long and about 8 to 10 inches wide with a fluid path having a width of about 0.75-1 inches. The inlet has an inside diameter of about 3/16 inch and is about ½ inch long. Any suitable length for secure connection to the tubing can be used. This design optimizes the appropriate amount of turbulence to ensure bacterial reduction while preventing cellular debris from building up on the surface of the UV bag. One advantage of this design is that it prevents cellular debris build-up on the surface of the bag which would otherwise occlude the transmission of the UV-C and prevent adequate bacterial reduction.

FIGS. 3A-E show various views of one embodiment of the UV system. The assembly consists of a UV grid lamp 303 and lamp support structure 301, comprising a lamp support 302. In one embodiment, the UV grid lamp 303 is supported in the UV lamp holder by buss wire 317. Quartz glass plates 305 are affixed to each side of the UV lamp holder with frames 306. A thermister 310 is held against the UV grid lamp 303 by a mounting block 309 to sense lamp temperature during use. Screws 311, 312, and 313 are provided as attachment means. Strain relief clamp 308 is provided to retain lamp wires. Hole 307 is provided as an alignment means. Hole 314 is provided as an attachment means. At least one spring 316 and one screw 315 is provided to hold the thermister mounting block 309 against the lamp 303 with spring force. An O-ring 304 is provided to seal the UV lamp 303 from any blood leakage in the event that irradiator bag leaks.

Figure 4:
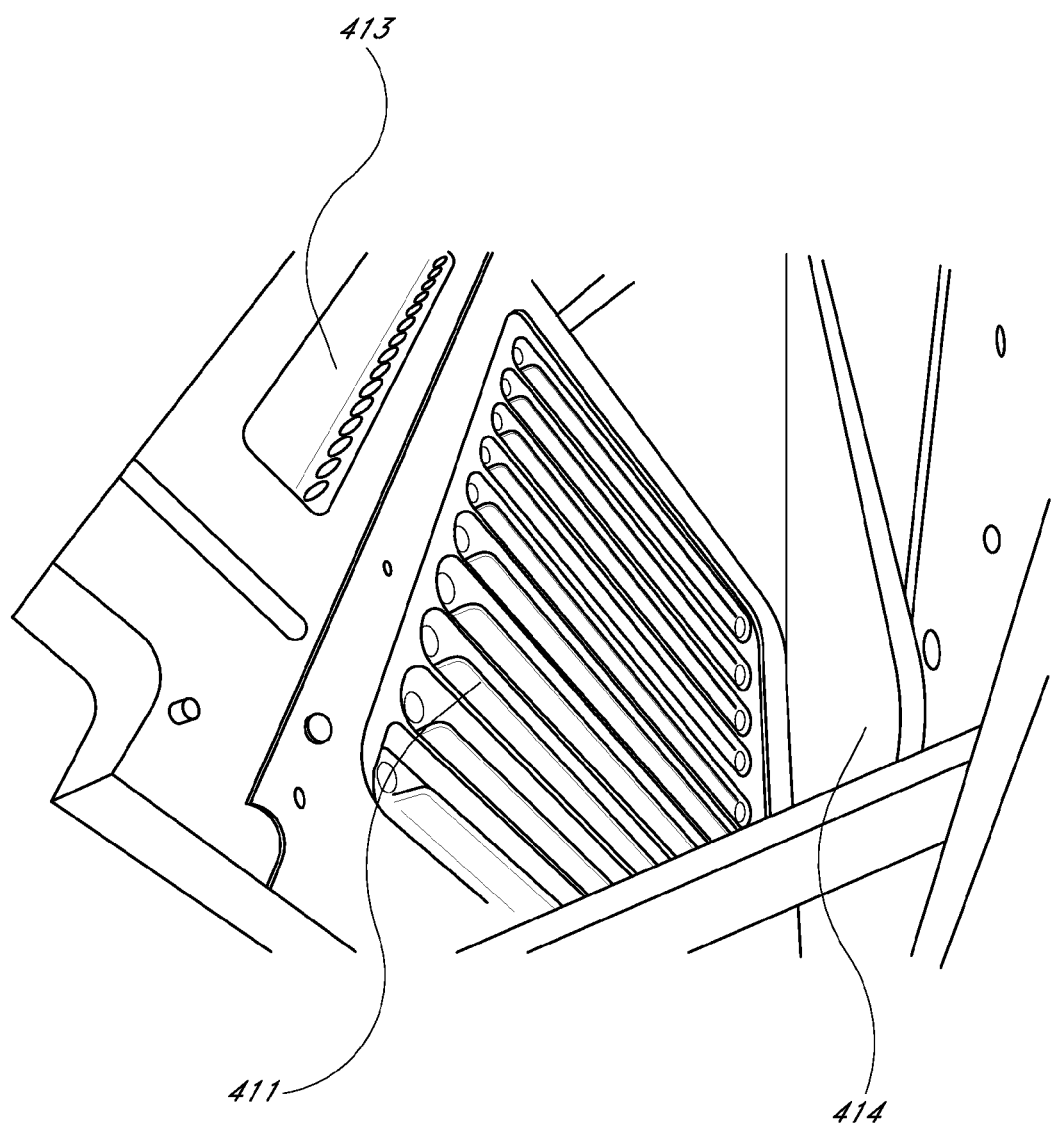
FIG. 4 shows the irradiator bag in open position.
Figure 5:
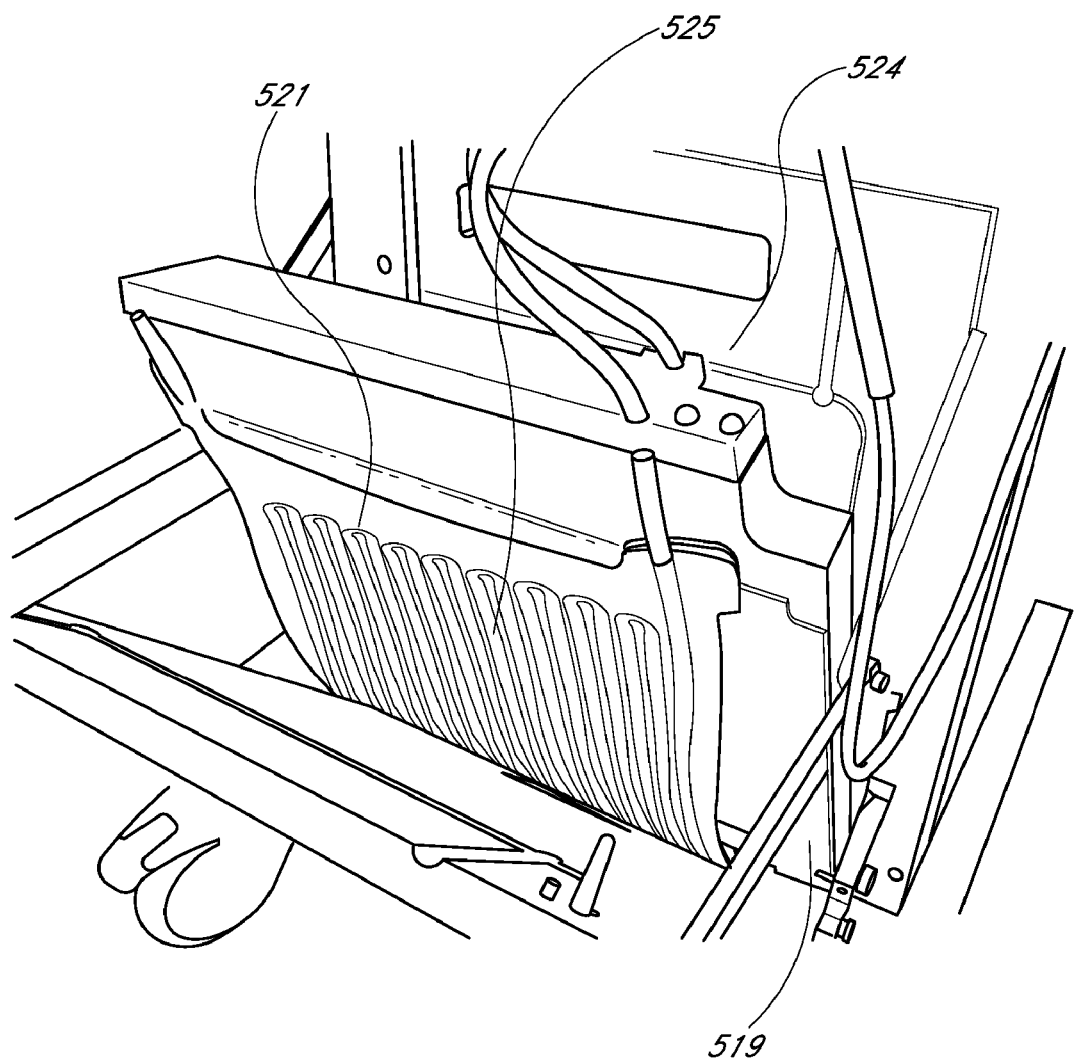
FIG. 5 shows the irradiator bag in closed position.

In one embodiment, the UV irradiator assembly is used to irradiate dilute extracorporeal blood with UV-C energy in the range of about 200-280 nm. In a preferred embodiment, UV-C light in the range of 254 nm is used. An open view of the irradiator is shown in FIGS. 4 and 5. In one embodiment, shown in FIG. 4, the assembly consists of a 200 W UV-C grid lamp 411 and lamp support structure 413, and two quartz glass plates (compression plates) to constrain the diluted blood in the irradiator bag to approximately 0.025" thickness. At least one UV-C sensor 414 is also provided. UV sensors and temperature sensors are used to optimize ultraviolet output of the bulb. In several embodiments, an optical sensor 414 for monitoring ultraviolet light during irradiation is used. According to data received from the sensor, the dose or intensity of UV light is adjusted. The UV light can be adjusted manually or adjustment can be automated. In one arrangement, electrical feedback control is provided from the sensor to the UV irradiator, thereby eliminating the need for manual control of light intensity.

In several embodiments, a safety interlock switch is provided to prevent unwanted user exposure to UV-C when loading/unloading the disposable set of materials. In one embodiment, the irradiator includes a conventional ultraviolet light source with a radiation wavelength of about 254 nm. One skilled in the art will understand that other suitable sources can also be used in accordance with several embodiments of the current invention. The UV source is connected to a suitable power source via a connector. The UV source is covered with a quartz plate which is used to compress the bag to allow maximum exposure of the blood solution. One skilled in the art will understand that plates made of any material that permits transmission of UV-C light can also be used in accordance with several embodiments of the present invention.

FIG. 5 also shows an irradiator in open position. In one embodiment, compression plates are hingedly attached to each side of the UV lamp holder by links 519. Air flow from the cooling duct 524 is used to keep the UV lamp at the proper temperature. A serpentine blood path 525 positioned within the irradiator bag 521 allows diluted blood to flow past the UV grid lamp.

Figure 6:
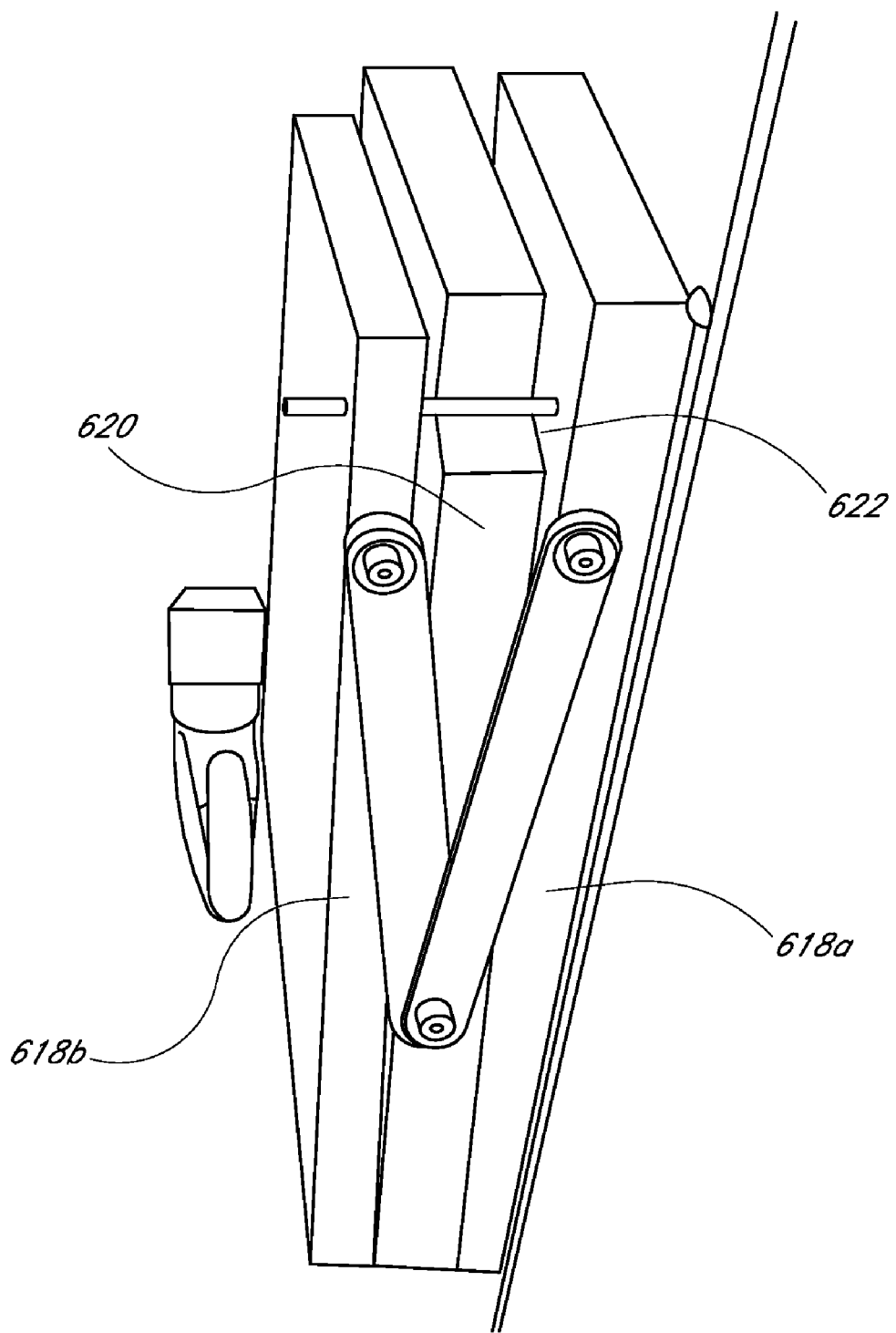
FIG. 6 shows the irradiator in open position.

A closed view of the irradiator is shown in FIG. 6. In one embodiment, the compression plates 618 are fastened to the UV lamp holder by thumbscrews 620. Compression plates 618 include inner 618*a* and outer 618*b* plates. The compression of the irradiator bag is set by the set screw 622. Lamp support structure is also shown 613.

In one embodiment, the UV assembly, including quartz plate, is mounted within an aluminum enclosure which is impermeable to UV light. In a preferred embodiment, the two quartz plates compress the blood within the bag to approximately 0.006-0.1 inches in order to establish a narrow space for blood flow therethrough. In one embodiment, a bag is placed on each side of the UV lamp. This configuration effectively doubles the UV-C exposure with a single grid lamp.

In one embodiment of the current invention, heparinized and possibly anti-oxidant or pharmaceutically treated blood in the extracorporeal circuit shown in FIG. 1 enters the inlet and passes through the serpentine path while a dose of approximately 1-50 mW/cm2 of UV-C, preferably 1-19 mW/cm2 of UV-C, more preferably 4-9 mW/cm2 of UV-C (the "effective" dose) is applied to the blood mixture. In one embodiment, the irradiator bag is placed between two quartz plates that compress (when closed) the diluted blood to about 0.025 inches in thickness, thereby facilitating the anti-microbicidal effect of the UV irradiator which delivers 1-50 mW/cm$^2$ of energy at 254 nm, preferably 2-20 mW/cm$^2$ of energy at 254 nm, more preferably 10-12 mW/cm$^2$ of energy at 254 nm.

Automation

In several embodiments, an on-line optical sensor for monitoring hematocrit during hemodialysis is used. These optical sensors are reported in the art (Jabara and Murta (1995), herein incorporated by reference). In this arrangement, electrical feedback control from such a sensor to pump 114 would eliminate the need for manual control at this point of the system.

In one embodiment, an electronic weight scale, or load cell 160, shown in FIG. 1, is provided. The load cell is used to measure or quantify the volume or mass of diluent. In one embodiment, a strain gauge beam-type load cell is used to measure the weight of the diluent bag. In one embodiment, the load cell is used to weigh the diluent bag continuously and control pump speeds. In one aspect, the load cell maintains a constant diluent weight, thereby maintaining return patient hematocrit at the same value as input patient hematocrit. In one embodiment, the diluent volume is kept constant at 750 mL in the diluent bag. One skilled in the art will appreciate that any given setpoint volume can be used.

Computer Hardware and Software

Figure 12:
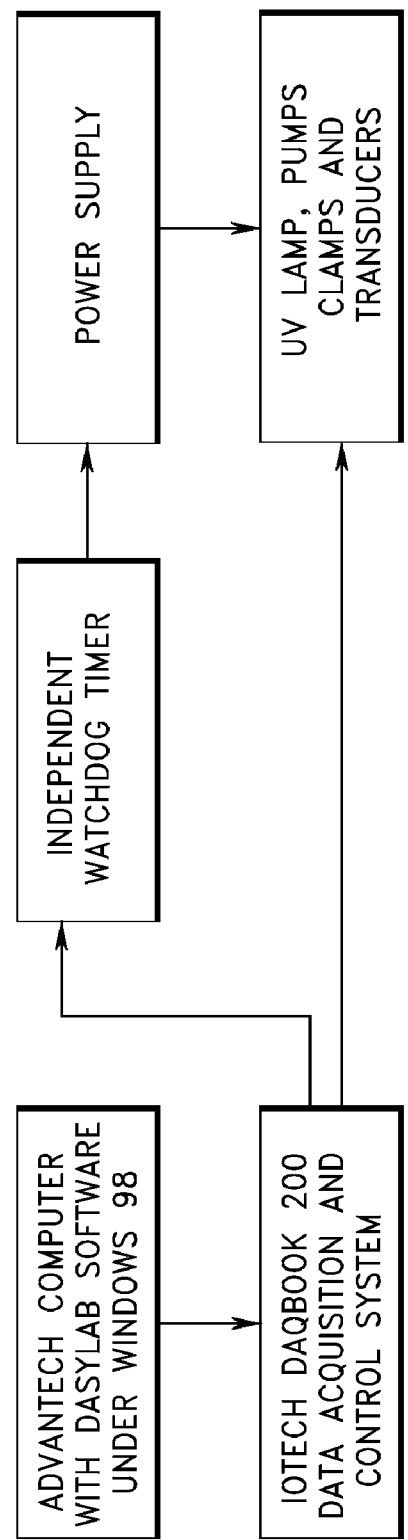
FIG. 12 shows a hardware/software scheme used in several embodiments of the invention.

Conventional computer hardware and software can be used with the HemaCharge™ (HemaVation, Costa Mesa, Calif.) device for clinical trials. In one embodiment, the HemaCharge system is a computer-controlled device running off-the-shelf (OTS) DasyLab® (National Instruments, Austin, Tex.) software under Windows® 98 (Microsoft, Redmond, Wash.). FIG. 12 shows an overview of one embodiment of the present invention.

In one embodiment, the hardware comprises an off-the-shelf Pentium-based based Advantech® computer with a color LCD display and touch screen connected to an off-the-shelf DaqBook200 (data acquisition and control system (Iotech Corporation). In one embodiment, the production device uses custom hardware and software. This system interfaces to pumps, clamps, ultraviolet lamp and transducers. In one embodiment, one or more pressure transducers or temperature sensors located at various points in the primary or secondary circuit are used as feedback for the software to ensure safe and optimal operation. In one aspect of the invention, the hardware includes an independent Watchdog Timer. If the OTS software or Windows 98 stops running, the Watchdog Timer is designed to turn off power to the lamp, pumps and clamps, which will stop flow, clamp blood lines and place the system into a safe mode. The clinical procedure would be stopped with a loss of approximately 250 mL of extracorporeal blood in the circuit, in the event of a failure.

User Operation

In one embodiment, four basic modes of operation are provided: (1) setup mode, (2) prime mode, (3) run mode, and (4) shut down mode.

Setup mode is used for loading a disposable set of materials, including spiking user-supplied diluent bag. The disposable set of materials includes one or more of the following: a hollow fiber filter used for hemoconcentrating dilute blood, one or two hollow fiber filters for cytokine removal, an irradiator bag assembly, and two additional bags (one for priming and one for containing diluent). During this mode, all pumps, clamps and alarms are disabled. Message prompts direct user through disposable set loading, input of patient hematocrit and blood volume, and calibration of pressure sensors.

The user initiates prime mode by depressing the appropriate key on the touch screen display, at which time both the primary and diluent circuits are primed, and the diluent bag will be filled to the proper level. Once filled, a heater 113*a* warms the contents of the diluent bag to normal body temperature. Once the circuit is primed, debubbled, and up to temperature, the clinician then pauses the system, and connects inlet and outlet lines to the patient catheter. In some embodiments, a heater or heat exchanger 108 is used to warm or cool at least some portion of the blood or diluent to between about 34° C. to about 42° C. In some instances, a heat exchanger 108 is used to warm or cool the blood temperature to body temperature prior to reintroduction into the patient. In some embodiments, a heater 108 is used to increase the temperature of at least a portion of the blood by about 1° C. to about 10° C.

Once priming is completed and patient is connected, the user initiates run mode, at which time primary circuit priming volume (~250 mL) is displaced by patient blood, and infused into the patient. During normal operation, patient blood is introduced to the device, diluted, irradiated, and hemoconcentrated back to the proper hematocrit before being returned to the patient.

At the end of the procedure, in shut down mode, the user pauses the system, disconnects the patient supply line and attaches it to the diluent bag. The user then resumes blood flow, displacing the remaining blood in the primary circuit with diluent, thereby returning extracorporeal blood to the patient. Pumps are stopped when diluent has displaced the blood in the return line. At this time, the catheter is removed from the patient and the disposable set of materials is discarded.

Bacterial Reduction and Cytokine Sieving

Figure 7:
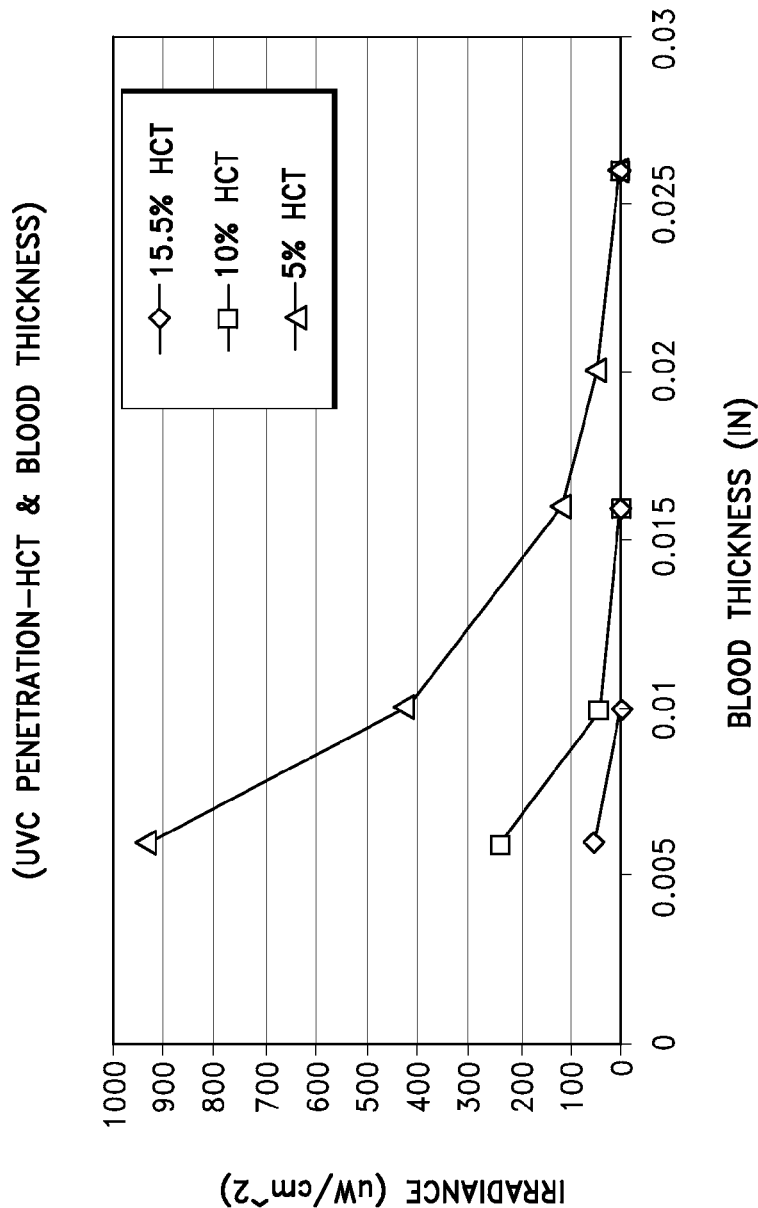
FIG. 7 shows UV-C penetration as a function of blood thickness.
Figure 8:
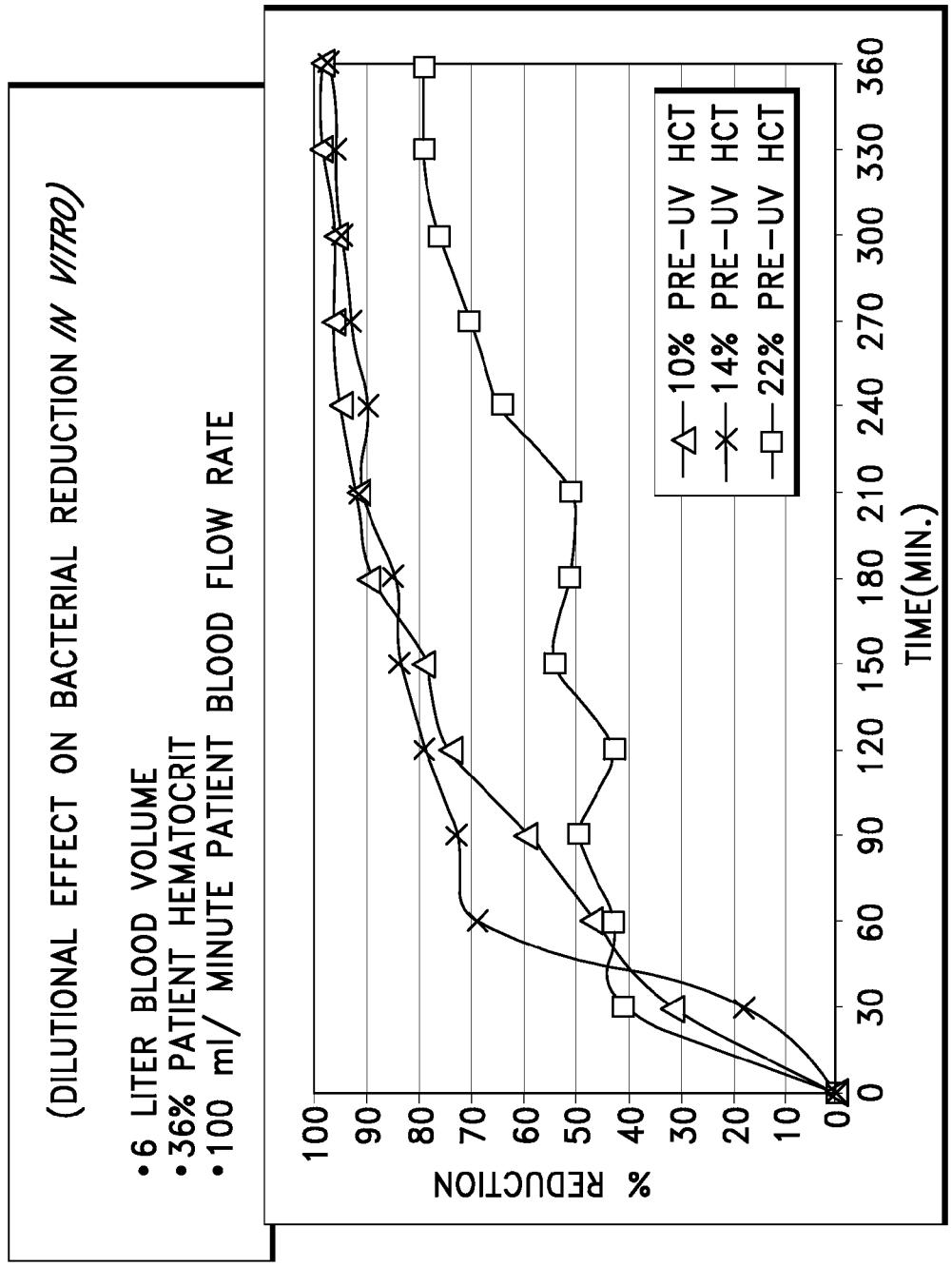
FIG. 8 shows dilutional effect on bacterial reduction in vitro.
Figure 9:
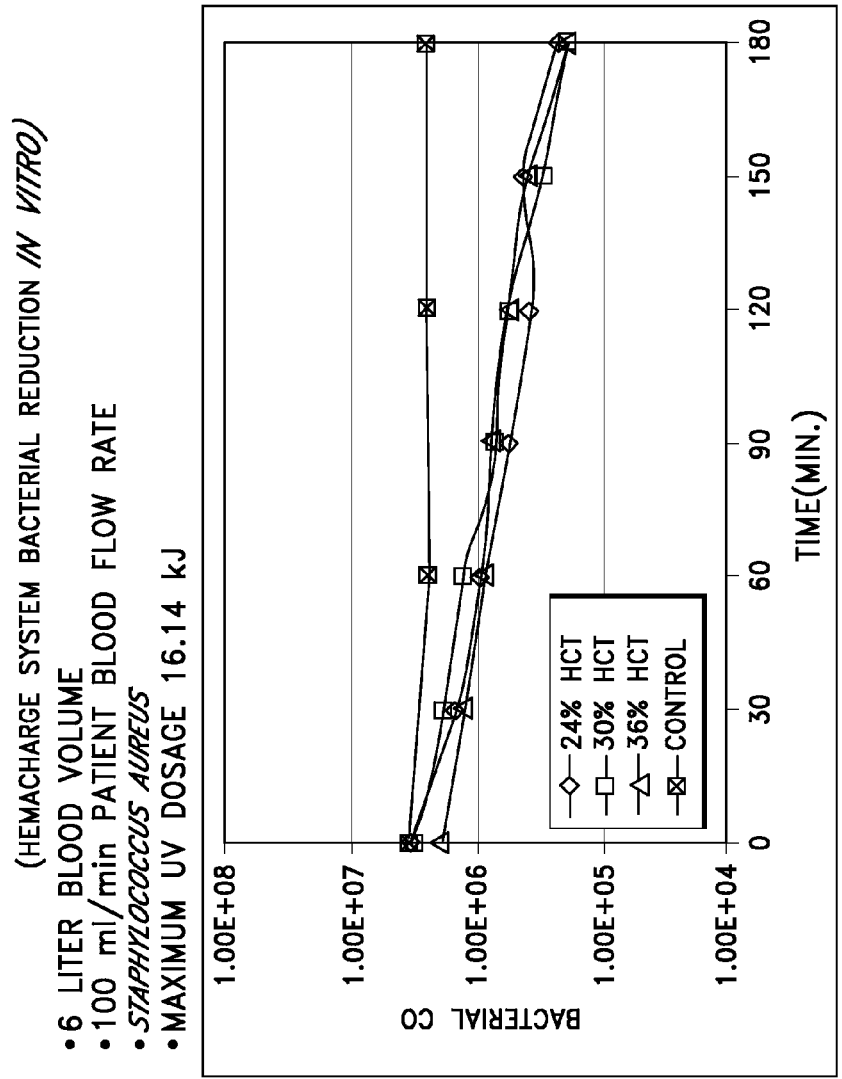
FIG. 9 shows bacterial reduction data at various hematocrits.
Figure 10:
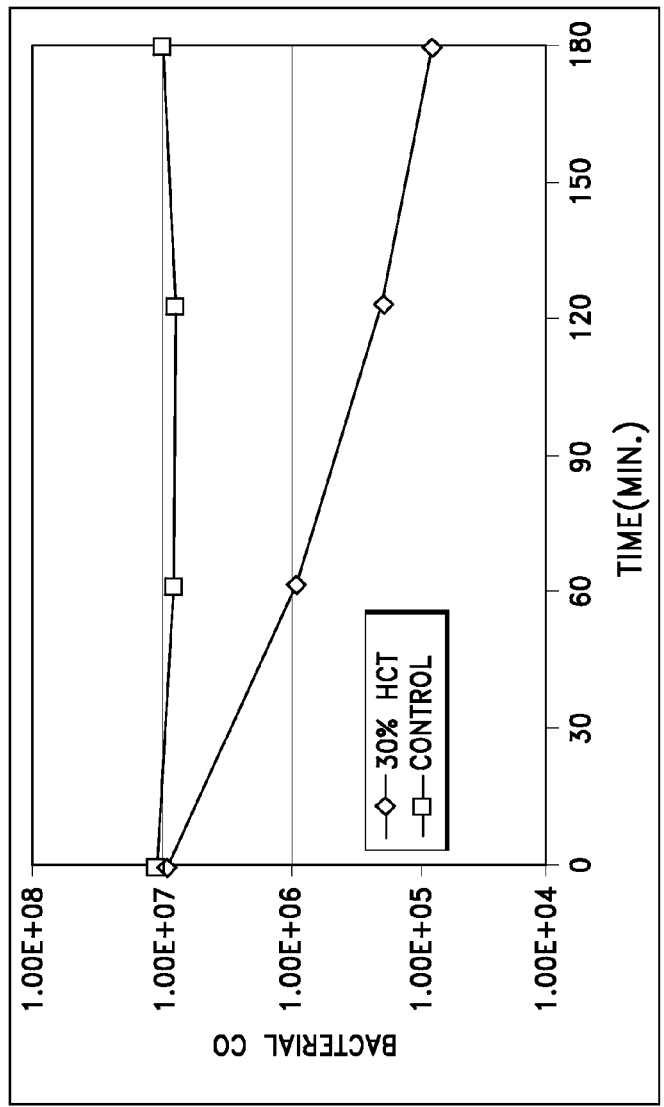
FIG. 10 shows bacterial reduction data at 30% hematocrit.
Figure 11:
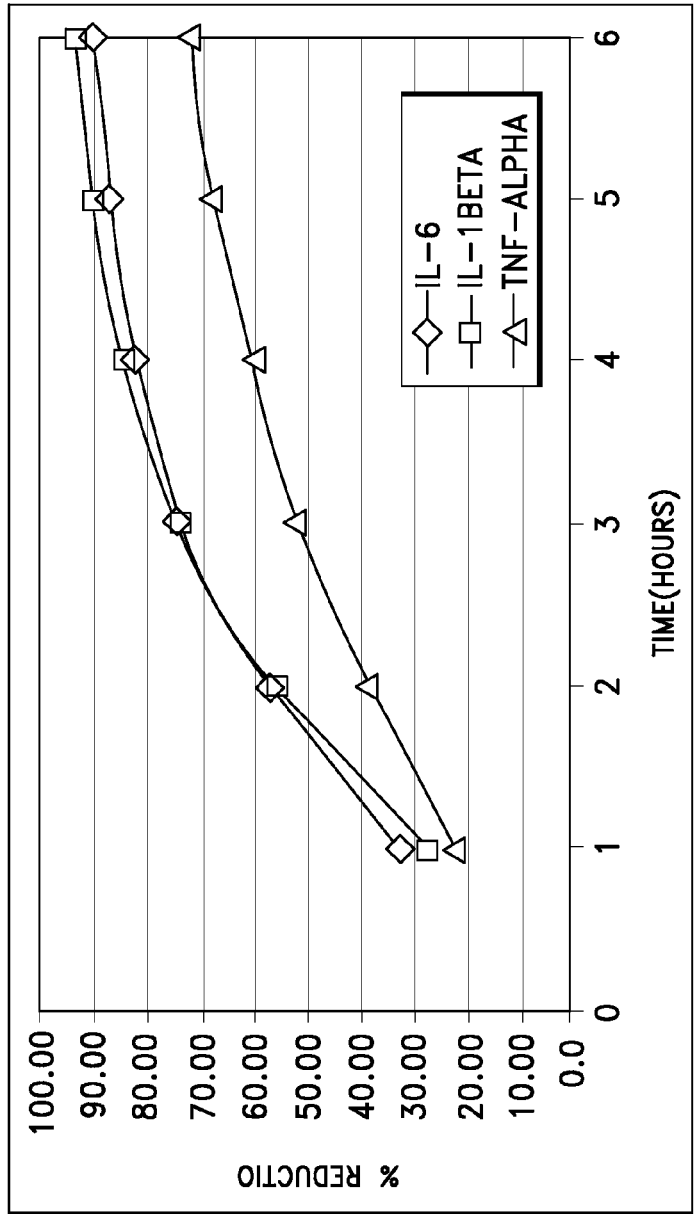
FIG. 11 shows cytokine sieving/reduction data in vitro.

In several embodiments of the current invention, a system is provided to reduce bacterial load in patient blood. In many embodiments, cytokines and other immune system mediators are removed. As used herein, the term "removed", and any tense thereof, shall be given its ordinary meaning, and shall also mean reduced in concentration, quantity and/or efficacy. FIG. 7 shows UV-C penetration as a function of hematocrit and blood thickness. FIG. 8 shows dilutional effect on bacterial reduction in vitro. FIG. 9 shows bacterial reduction data at various patient hematocrits in the HemaCharge system at 6 L blood volumes. FIG. 10 shows bacterial reduction data at 30% patient hematocrit at 3 L blood volumes. FIG. 11 shows cytokine sieving/reduction data in vitro at 6 L blood volumes. In one embodiment of the present invention, diluted blood passes through tubing to the bactericidal ultraviolet (UV) irradiation device, shown schematically in FIGS. 2A-D. Controlled in vitro experiments have demonstrated that UV irradiation penetrates the blood more effectively when whole blood (26-55% hematocrit) is diluted to a hematocrit of about 5-20% (see FIG. 7) thus translating into a more efficient microbicidal activity (see FIG. 8). Further, when diluted blood is presented to the hemoconcentrator 106, target molecules are more effectively removed by sieving. In many embodiments of the current invention, toxic targets, such as bacteria and immune system mediators, are removed from a patient's blood without using ultraviolet light irradiation. In some of these embodiments, a series of hemoconcentrators and filters are used to reduce pathological targets in blood. Immune system mediators, include, but are not limited to, inflammatory mediators. Inflammatory mediators include, but are not limited to, TNF, IL-1β, IL-6, IL-8, IL-10, IL-12, LPB, IFNγ, LIF, MIF, MCP-1, C3-a, C5-a, exotoxins and endotoxins. In one embodiment, the concentration of at least one inflammatory mediator is reduced by about 75% in less than about 4 hours using embodiments of the current invention. In another embodiment, the concentration of TNF-α is reduced by about 50% in less than about 4 hours.

Vitamin Therapy

Vitamin therapy is used in several embodiments of the current invention as an adjunctive therapy. In several embodiments, a system and method of reducing toxins in a patient's blood using vitamin therapy is provided. These vitamins include the free radical quenchers and antioxidants described below, and also include several vitamins which exert their action by reducing the concentration of toxins, including, but not limited to bacteria, viruses, free radicals and inflammatory mediators, in the blood. In one embodiment, vitamins are added to the blood prior to, during and/or after treatment with the concentrator/filter embodiments described herein. Vitamins are administered directly to the patient and/or are added to the various components of the concentrator/filter embodiments, including, but not limited to, the tubing, the pump, the filters and the diluent source so that the blood can be exposed to the vitamins while being concentrated or filtered using this system. Antioxidants and free radical quenchers administered in several embodiments of the current invention, include, but are not limited to, Zn, Cu, manganese, selenium, vitamin A, C, E, B complex, K, P, lycopene, superoxide dismutase, co-enzyme Q10, catechins, polyphenols, flavanols, depsides (chlorogenic acid, coumaroylquinic acid and theogallin), quinic acids, carotenoids, thearubigens, theaflavin and theaflavic acids are used to reduce bacterial load in blood processed by several embodiments of the current invention. In one embodiment, a combination of Vitamin A, C, E and zinc is used. In one embodiment, naturally-occurring and/or synthetic theaflavin is used. In one embodiment, ethyl pyruvate, a chemical additive with anti-oxidant properties, is used. One skilled in the art will be able to determine the appropriate dose of antioxidants, to be administered. In one embodiment, doses are adjusted per blood volume to yield maximum plasma concentration values (Cmax) of about 1 pg/mL plasma to about 1 mg/mL plasma per individual component. Preferably, doses to achieve Cmax values of about 10 ng/mL to about 1000 ng/mL are provided. In one embodiment, the following plasma concentrations are used: Vitamin B12 at 0.2-0.5 mg/mL, Vitamin E at 0.13 IU/mL, Vitamin C at 0.16 mg/mL, Vitamin P at 0.65 mg/mL, Vitamin A at 0.02 IU/mL and Vitamin K 0.003 mg/mL.

In one embodiment, one or more vitamins are added to the blood while the blood is being processed through the system of the current invention. In other embodiments, patients are treated with a vitamin cocktail prior to treatment using the present invention. In some embodiments, patients are given the vitamin cocktail after their blood has been treated with the present invention in order to maintain a reduced cytokine and/or bacterial load. In some embodiments, vitamin therapy is administered in between treatments. Extracorporeal blood may also be treated at any time before, during or after treatment with the system of the current invention. In embodiments in which vitamin therapy is provided simultaneously with treatment by the system of the current invention, one or more vitamins are pre-mixed with the diluent. In another embodiment, a vitamin cocktail is added to the pump, so that the vitamins and blood and/or diluent mix with the vitamins during processing. One of skill in the art will understand that vitamins can be added at any stage and in any component of the current blood treatment system.

In one embodiment, pharmacological therapy is administered in substantially the same way as described above for vitamin therapy. In one embodiment, insulin therapy is provided to facilitate cellular glucose entry for improved mitochondria performance. One skilled in the art will appreciate that other drugs which facilitate cellular glucose entry and/or for improving mitochondria performance can also be used in accordance with several embodiments of the current invention. In another embodiment, nitroglycerin is provided to improve microcirculation in order to improve organ oxygenation. One skilled in the art will appreciate that other drugs which improve microcirculation can also be used.

In several embodiments, vitamin therapy is used in conjunction with a UV irradiator. In one embodiment, antioxidants and other free radical quenchers are used to reduce free radicals which may be produced by the UV light and as a result of typical sepsis-induced cell damage. In some embodiments, the vitamins used to treat the blood to prevent activation of cells which initiate build-up on the surface of the UV bag and occlude the transmission of the ultraviolet light. One skilled in the art will appreciate that pharmaceuticals, chemicals or other agents can also be used instead of, or in addition to, the anti-oxidants and quenchers described herein. In one embodiment, the UV-C facilitates the penetration of pharmaceutical agents into cells more effectively by activating cell membranes to increase permeability.

EXAMPLES

The following Examples illustrate various embodiments of the present invention and are not intended in any way to limit the invention.

Example 1

The HemaCharge Device

Figure 13:
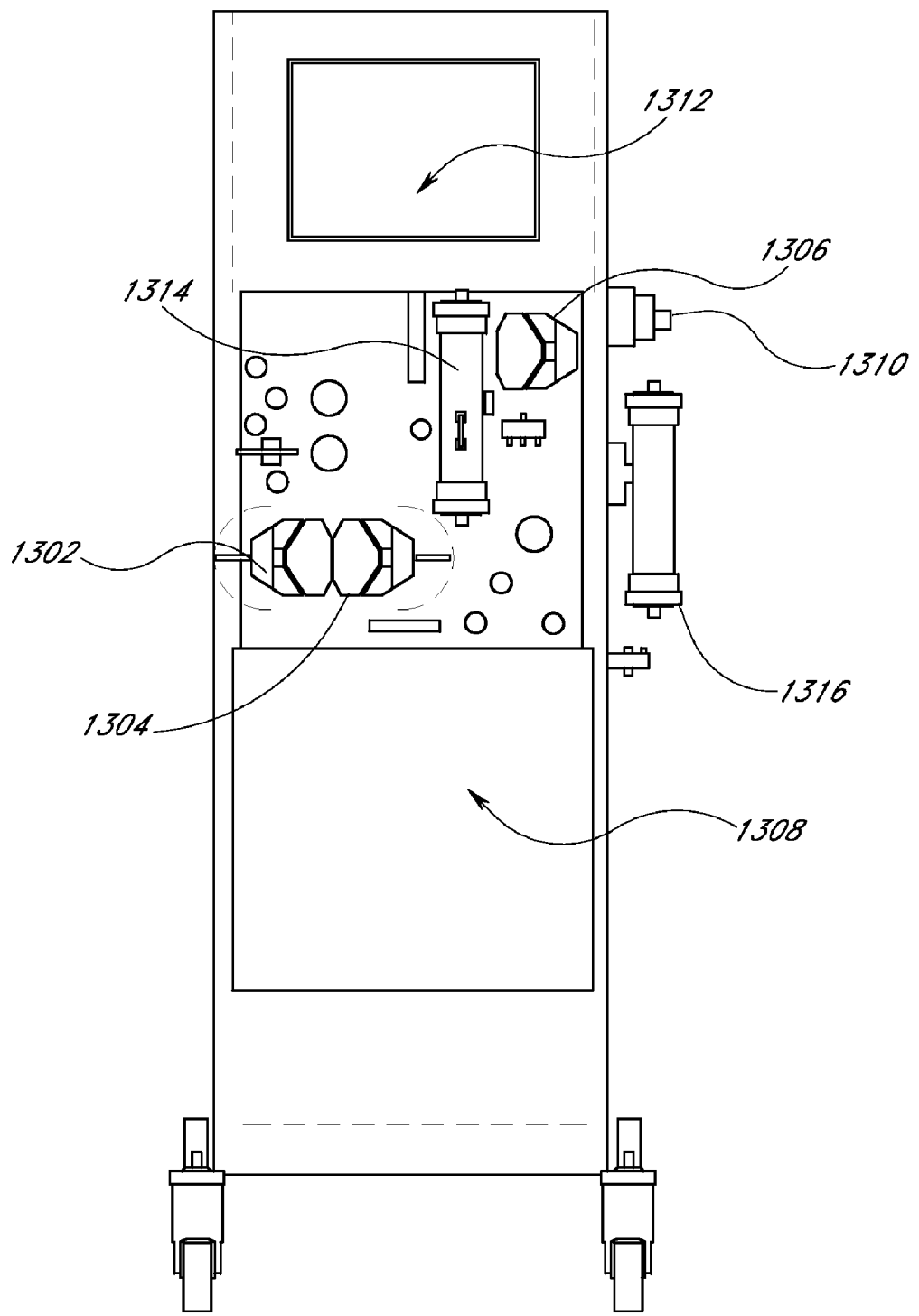
FIG. 13 shows a physical embodiment of the HemaCharge System.

In one embodiment of the current invention, shown in FIG. 13, an embodiment referred to as "the HemaCharge device" is provided. In this embodiment, the system comprises three pumps (blood pump 1302, diluent pump 1304, and hemoconcentrator pump 1306), an ultraviolet irradiator lamp assembly 1308 and a load cell 1310 to maintain proper hemodilution and hemoconcentration of patient blood. The user interface is a backlit LCD touch screen display 1312. The device also incorporates clamps, a bubble detector, pressure sensors, temperature sensors, a UV sensor, as well as visual and audible alarms for patient safety. A power supply module is provided containing an isolation transformer, a solid-state electronic ballast, and associated electronics to produce about 5-24 VDC to power the pumps, clamps, and sensors. A strain gauge beam type load cell is provided to measure the weight of the diluent bag. A 70-90 kD polysulfone hollow fiber filter 1314 used for hemoconcentrating dilute blood and two 10 kD polysulfone hollow fiber filters 1316 for cytokine removal are also provided.

The UV irradiator assembly 1308 is used to irradiate dilute extracorporeal blood with 254 nm UV-C energy. The assembly consists of a 200 W UVC grid lamp and lamp support structure, two quartz glass plates and compression plates to constrain the diluted blood in the irradiator bag to approximately 0.025" thickness, and UV-C and temperature sensors to optimize ultraviolet output of the bulb. A safety interlock switch is provided to prevent unwanted user exposure to UV-C when loading/unloading the disposable set of materials.

The three pumps consist of a blood pump 1302 for pumping whole blood from the patient to the irradiator, a diluent pump 1304 for introducing diluent into the whole blood before the irradiator, resulting in hemodilution to about 10% HCT, and a concentrator pump 1306 used to provide a transmembrane pressure across the 70-90 kD filter 1314 for hemoconcentration before returning blood to the patient. Pump control is accomplished by using proportional-integral-differential (PID) feedback loops from encoders located on each pump motor, along with pump ratio parameters calculated from user input of HCT and blood flow rate.

Three clamps are provided: one each on the patient inlet and outlet lines for patient isolation and safety, and a third clamp to allow by-passing of the cytokine filter 1316 for discontinuance of cytokine filtration. The bubble detector is located immediately before the patient return line clamp for protection against returning air emboli to the patient.

Five pressure sensors are used; one each on the patient inlet and return lines, one before the irradiator bag assembly inlet, one at the hemoconcentrator inlet, and one located between the hemoconcentrator ultrafiltrate outlet and the concentrator pump 1306. The inlet pressure sensor can be used to determine maximum allowable blood flow rate based on vascular access and catheter placement parameters; the patient return line sensor can likewise indicate catheter placement issues on the return side, as well as provide a measure of safety against excessive return pressures. The sensor located before the irradiator bag assembly provides an indication of bag pressure and is used to prevent over pressurization of the irradiator bags. The sensors located at the inlet and ultrafiltrate outlet of the hemoconcentrator 1306 as well as the patient return sensor can be used together to determine hemoconcentrator TMP. TMP can be used to determine appropriate blood flow rates and to determine adequate performance of the hemoconcentrator 1306. Visual and audible alarms are provided for out-of-range pressures.

Temperature is sensed at one or more of the following locations in the circuit: patient inlet and outlet, irradiator bag assembly outlet 1308, and on the diluent bag. Additionally, the UV lamp temperature is also monitored for optimization of UVC output. Sensors in the extracorporeal circuit are used to assure a safe blood temperature throughout the circuit. Visual and audible alarms are provided for out-of-range temperatures.

Computer hardware and software, described substantially as above, is used with the HemaCharge device.

In one aspect of the HemaCharge device, a disposable set of materials is provided. The disposable set comprises a 70-90 kD polysulfone hollow fiber filter 1314 used for hemoconcentrating dilute blood, one or two 10 kD polysulfone hollow fiber filters 1316 for cytokine removal, an EVA irradiator bag assembly, and two PVC bags; one for priming and one for containing diluent. Although one skilled in the art will understand that several filters can be used in accordance with various embodiments of the present invention, polysulfone hemofilters are particularly advantageous because of their biocompatibility and because they absorb serum factors associated with complement factor C3bi expression on neutrophils and monocytes. In some embodiments, electrostatically charged, melt-blown material, such as polypropylene, can be used. The disposable set also incorporates a bubble trap, two injection sites for administering medications, and the required tubing interfaces for the pressure and temperature sensors. Catheters and diluent for priming are user-supplied items. All tubing is PVC, and disposable sets are tested for biocompatibility and sterility before initiation of treatment.

Example 2

In Vitro Studies

Over one thousand in vitro experiments have been conducted to date using several embodiments of the present invention. Factors investigated included appropriate UV transparent material, hematocrit of blood for optimal UV absorption, ideal blood flow path for adequate UV exposure, ideal UV dosage, ideal pore size of hemofilters, ideal surface area of hemofilters, ideal blood model, development of porcine cytokine assays, various circuit coatings and optimal flow rates.

FIGS. 8-10 show data from bacterial reduction studies. In one embodiment, a logarithmic base ten reduction (90%) of *Staphylococcus aureus* (ATCC 6538p) was provided within three hours and in some instances a two logarithmic base ten (99%) reduction within six hours of UV-C exposure. *Staph. aureus* was selected as the bacterial model because it is one of the most common organisms associated with sepsis and because it is considered one of the most difficult to kill. One skilled in the art will understand that other bacteria can also be effectively reduced in accordance with several embodiments of the current invention. FIG. 9 demonstrates a series of 36 bacterial reduction experiments conducted at a blood volume of 6 liters. The maximum UV dosage was 16.14 kJ. Patient blood flow rate was 100 mL/min. 31 UV experiments and 5 controls were performed. FIG. 10 demonstrates a series of 8 bacterial reduction experiments conducted at a blood volume of 3 liters. The maximum UV dosage was 12.90 kJ. Patient blood flow rate was 100 mL/min. 5 UV experiments and 3 controls were performed.

These in vitro experiments were conducted with three or six liters of fresh bovine whole blood anti-coagulated with EDTA. To allow for the UV to penetrate the blood and to facilitate the efficient sieving of middle molecular weight molecules, the blood was diluted to 10% prior to entering the irradiator and then re-concentrated to the starting hematocrit via the 85 kD hemoconcentrators. Bovine blood anti-coagulated with EDTA was chosen as the blood model because it is an industry accepted standard for evaluating hemofilters and because it is less subject to daily variations. Each experiment used a breadboard-UV irradiator at a patient blood flow rate of 100 mL/min. Additionally, controls were conducted without the UV-C light to determine how the system and fresh blood affect the level of bacterial reduction alone. As indicated in the graphs, the UV-C energy was responsible for the 90% reduction of bacteria. Other studies were conducted at various blood volumes, flow rates and patient hematocrits and resulted in at least a 90% reduction in *Staph. aureus*.

FIG. 11 shows data from cytokine sieving, or reduction, studies. Typically, cytokine reduction studies have been conducted on TNF-α, IL-1β and IL-6 because these cytokines have been well-established as markers for sepsis. Additionally, down-regulating the immune system, as opposed to suppressing it completely, may be important in treatment. A 50-75% reduction in key inflammatory mediators can reverse the exaggerated immune response and allow the immune system to become effective again. FIG. 11 shows several embodiments of the current invention provide at least a 50-75% clearance of all three target molecules within three hours. Cytokine studies were conducted as described above for the bacterial reduction experiments Additional studies have been conducted at various blood volumes, flow rate and patient hematocrits. One skilled in the art will understand that in various embodiments of the current invention, the current system will be able to remove several cytokines and cell mediators, including, but not limited to, TNF-α, IL-1β, IL-6, IL-10, IL-12, LPB, IFNγ, LIF, MIF, MCP-1, C3-a, C5-a, exotoxins and endotoxins.

Example 3

In Vivo Studies

Over eighty animal studies have been conducted in accordance with several embodiments of the current invention. Variables investigated included appropriate animal models, effects of UV dosage, maintaining a pig under anesthesia for up to 16 hours, ideal flow rates, various circuit coatings, various anticoagulants and various replacement fluids. The cell safety data represents 16 animal trials encompassing four different safety models: Sham, Tubing Control, UV Control and Experimental. All trials were conducted on 50-68 kg SPF Yorkshire pigs anesthetized and in recumbent position. Venous blood supply was obtained by way of a femoral vein cut-down and blood pressure was monitored via the femoral artery. Each subject was monitored for at least one week post-treatment. The following is a brief description of each model:

In the sham model, a 12 french double lumen catheter was placed in the femoral vein and the subject was monitored for six hours.

In the tubing sham model, the technique was similar to the sham model, with the addition of a simple extracorporeal circuit composed of dialysis tubing with an equivalent extracorporeal volume of the system and one blood pump set to 100 mL/min.

In the control model, the breadboard system was run for six hours at a patient blood flow rate of 100 mL/min without exposing the blood to UV-C.

In the experimental model, the complete breadboard system was run for six hours at a patient blood flow rate of 100 mL/min while exposing the blood to UV-C.

The data for all models demonstrated that the white blood cell counts decreased during the first 60 minutes of the procedure, and tended to increase thereafter. The control model had the lowest six-hour white blood cell count; however, this sample was only slightly lower than the experimental model. Thus, the current system is the major factor affecting the white blood cell count, which is a typical response to extracorporeal circulation. The UV-C was not a significant factor in the decrease. The increase in post-treatment white blood cell counts is a typical response to anesthesia and extracorporeal devices. Ultimately, the one-week (168 hr) sample for all models demonstrated essentially the same white blood cell counts, indicating that the effect of the circuit was temporary.

The red blood cell counts remained relatively stable throughout the treatment and recovery periods of all models. Overall, the circuit and the UV-C did not have an effect on the red blood cell counts.

The platelet counts typically exhibited a downward trend throughout the treatment period for the control and experimental models. The experimental model typically had the lowest overall six-hour platelet count. This count, however, was well above the safety cut-off level of 50,000 platelets per deciliter. The decrease observed in both models indicated that the system's circuit and the UV-C each had an effect on the subject's platelet levels. All platelet counts for each model increased to above-normal levels within 48 hours following treatment as a typical response to anesthesia and extracorporeal devices. Ultimately, the one-week (168 hr) sample for all models demonstrates platelet counts within the normal range. This indicates that the effect of the circuit and UV-C are temporary. Other cell damage data collected are described and discussed below.

A methemoglobin assay was used to determine the level of damage to the hemoglobin molecule. A value less than 2% of the total concentration of hemoglobin in the blood is considered normal. All the samples were well within the normal range and did not significantly increase throughout the treatment. This indicates that the UV-C, at the given dosage, is not causing any significant damage to the hemoglobin molecule.

A white blood cell viability dye exclusion assay was used to determine whether a white blood cell is viable due to damages to the DNA and cell membrane. If a cell takes in the dye, that cell is considered non-viable. Less than or equal to 10% overall reduction from the baseline value is considered normal. All of the samples for each model were within the normal range. This indicates that the circuit and UV-C were not causing any damage to the cells.

A red blood cell osmotic fragility assay was used to determine any cell membrane damage that could cause future lyses when returned to the subject. Permeability of erythrocyte cell membranes is a factor to consider after UV irradiation. A sample of blood is mixed with a 0.9% isotonic solution of saline and distilled water is added to the blood mixture until lyses is observed. The results are represented as the saline concentration at which the first cells begin to lyses (Initial Osmotic Fragility) and the saline concentration at which all of the cells are lysed (Complete Osmotic Fragility). The normal range for Initial Osmotic Fragility is 0.50-0.59% saline. The normal range for Complete Osmotic Fragility is $\leq 0.50\%$ saline. All of the samples for each model were within the normal range. This indicates that the circuit and UV-C were not causing any damage to the cells.

Platelet activation assays were used to determine the level of platelet activation. The assays are listed in order of platelet activation level: Platelet CD62P, Platelet Bound Fibrinogen, Monocyte-Platelet Aggregates and Neutrophil-Platelet Aggregates. Samples for each assay were taken across the circuit at the following locations: From Subject, Pre-UV, Post-UV and Post-Hemoconcentrators. For every assay, the level of activation increased as the cells moved through the circuit. In other words, diluting, irradiating and hemoconcentrating the blood had a contributing and cumulative effect on platelet activation. In particular, the Leukocyte-Platelet Aggregates at the six-hour sample were up to levels seen in cardiopulmonary bypass systems.

At the current dosage of UV-C, platelets were the only cells that were significantly affected. However, it is important to note that none of the platelet levels from any of the safety models discussed above would have prompted a physician to supply replacement donor platelets to a human patient (i.e., less than about 50,000 platelets/dl).

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A method of treating a patient infected with a virus, comprising:
   removing at least a portion of the patient's virus-infected blood;
   diluting said at least a portion of the blood with a diluent to provide diluted blood, thereby reducing a viral concentration in said at least a portion of the blood;
   irradiating at least a portion of the diluted blood using a UV light source;
   concentrating the diluted blood using a hemoconcentrator thereby removing at least a portion of the diluent therefrom;
   returning the treated blood to the patient,
   wherein irradiating at least a portion of the diluted blood comprises providing a fluid chamber adjacent to the UV light source, said fluid chamber confining the diluted blood to a thin film for exposure to said UV light source;
   wherein a portion of the diluted blood is transported through a serpentine path during irradiation;
   wherein the UV light source is configured to directly inactivate or kill one or more viruses in the diluted blood while the diluted blood is transported along a serpentine path within the fluid chamber.

2. The method of claim 1, further comprising filtering the diluted blood to remove one or more viruses from said diluted blood.

3. The method of claim 1, further comprising oxygenating the blood received from the patient.

4. The method of claim 1, further comprising adding at least one vitamin to the at least a portion of the patient's virus-infected blood to further target the deactivation or destruction of viruses present within said blood.

5. The method of claim 1, further comprising heating or cooling the blood to about body temperature.

6. The method of claim 1, further comprising heating or cooling the blood to between about 34° C. to about 42° C.

7. The method of claim 1, further comprising returning the diluent removed from the blood to a diluent source via a recycle path.

8. The method of claim 7, wherein said recycle path comprises a recycle path filter.

9. A method of treating a patient infected with a virus, comprising:
   removing at least a portion of the patient's virus-infected blood;
   filtering said virus-infected blood to remove one or more viruses from said blood, thereby producing treated blood;
   heating or cooling the blood to about body temperature;
   returning the treated blood to the patient;
   diluting at least a portion of the blood with a diluent to provide diluted blood, thereby reducing a concentration of viruses in said at least a portion of the blood;
   irradiating at least a portion of the diluted blood using a UV light source; and
   concentrating the diluted blood using a hemoconcentrator thereby removing at least a portion of the diluent therefrom.

10. The method of claim 9, wherein irradiating at least a portion of the diluted blood comprises providing a fluid chamber adjacent to the UV light source, said fluid chamber confining the diluted blood to a thin film for exposure to said UV light source,
    wherein concentrating the diluted blood using a hemoconcentrator thereby removing at least a portion of the diluent therefrom;
    wherein a portion of the diluted blood is transported through a serpentine path during irradiation; and
    wherein the UV light source is configured to directly inactivate or kill one or more viruses in the diluted blood while the diluted blood is transported along a serpentine path within the fluid chamber.

11. The method of claim 9, further comprising oxygenating the blood received from the patient.

12. The method of claim 9, further comprising adding at least one vitamin to the at least a portion of the blood to further target the deactivation or destruction of viruses present within said blood.

13. The method of claim 9, wherein the blood is thermally conditioned to between about 34° C. to about 42° C.

14. A method of treating a patient infected with a virus, comprising:
    removing at least a portion of the patient's virus-infected blood;
    irradiating at least a portion of the blood using a UV light source;
    wherein the UV light source is configured to directly inactivate or kill one or more viruses in the diluted blood while the diluted blood is transported along a serpentine path of a fluid chamber;
    filtering at least a portion of the blood to remove one or more viruses from said blood, thereby producing treated blood; and
    returning the treated blood to the patient.

15. The method of claim 14, further comprising adding at least one vitamin to the at least a portion of the blood to further target the deactivation or destruction of viruses present within said blood.

16. The method of claim 14, further comprising oxygenating the blood received from the patient.

17. The method of claim 14, further comprising thermally-conditioning the blood to about body temperature.

18. The method of claim 14, further comprising heating or cooling the blood to between about 34° C. to about 42° C.

* * * * *